（12）United States Patent
Doi et al.

(10) Patent No.: US 12,329,502 B2
(45) Date of Patent: Jun. 17, 2025

(54) BLOOD PRESSURE MEASUREMENT CUFF AND METHOD FOR MANUFACTURING SAME

(71) Applicant: OMRON HEALTHCARE Co., Ltd., Muko (JP)

(72) Inventors: Ryosuke Doi, Kyoto (JP); Minoru Taniguchi, Kyoto (JP); Takayuki Matsuoka, Kyoto (JP); Takayuki Shiina, Kyoto (JP); Yo Imai, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 713 days.

(21) Appl. No.: 17/573,749

(22) Filed: Jan. 12, 2022

(65) Prior Publication Data

US 2022/0133160 A1    May 5, 2022

Related U.S. Application Data

(63) Continuation of application No. PCT/JP2020/026780, filed on Jul. 9, 2020.

(30) Foreign Application Priority Data

Jul. 18, 2019    (JP) .................... 2019-132816

(51) Int. Cl.
*A61B 5/022*    (2006.01)
*B29C 65/72*    (2006.01)
*B29L 31/00*    (2006.01)

(52) U.S. Cl.
CPC .......... *A61B 5/02233* (2013.01); *B29C 65/72* (2013.01); *A61B 2562/12* (2013.01); *B29K 2713/00* (2013.01); *B29L 2031/753* (2013.01)

(58) Field of Classification Search
CPC ..... A61B 5/02233; A61B 5/021; A61B 5/022; A61B 5/02241; B29C 65/72;
(Continued)

(56) References Cited

U.S. PATENT DOCUMENTS 8,652,057 B2 *   2/2014   Vivenzio ............ A61B 5/02233
                                                              600/490
2010/0268100 A1 * 10/2010  Nakanishi .......... A61B 5/02233
                                                              600/499

FOREIGN PATENT DOCUMENTS

JP    55-134806 U1    9/1980
JP    59-183206 U1    12/1984
(Continued)

OTHER PUBLICATIONS

International Preliminary Report on Patentability with English translation issued on Feb. 3, 2021, in corresponding International Application No. PCT/JP2020/026780; 6 pages.
(Continued)

*Primary Examiner* — Eric F Winakur
*Assistant Examiner* — Noah M Healy
(74) *Attorney, Agent, or Firm* — Maier & Maier, PLLC

(57) ABSTRACT

A blood pressure measurement cuff includes a belt-like body including an outer fabric and an inner fabric facing each other to form a bag shape, the belt-like body housing a fluid bag, an elliptical ring member having one side attached to a region adjacent to one end of the belt-like body, a retaining member provided to a region adjacent to the other end of the belt-like body, and a fixing member provided to a front surface of the outer fabric of the belt-like body. The retaining member includes a projection part that is flexible and projects outward of the belt-like body in a thickness direction Z, and support parts, each being flat plate-like, contigu-
(Continued)

ous with a base of the projection part, and attached along the region adjacent to the other end of the outer fabric.

5 Claims, 21 Drawing Sheets

(58) Field of Classification Search
CPC ... B29K 2713/00; F16G 11/12; B60R 22/357; B60R 22/38; B60R 22/42; B60R 22/1855; A42B 3/08; A01K 27/001; A43C 11/1413
See application file for complete search history.

(56) References Cited

FOREIGN PATENT DOCUMENTS

| | | |
|---|---|---|
| JP | 5-35103 U1 | 5/1993 |
| JP | 2010-252836 A | 11/2010 |
| JP | 2013-34791 A | 2/2013 |

OTHER PUBLICATIONS

Translation of International Search Report dated Oct. 6, 2020 in corresponding International Application No. PCT/JP2020/026780; 2 pages.

* cited by examiner

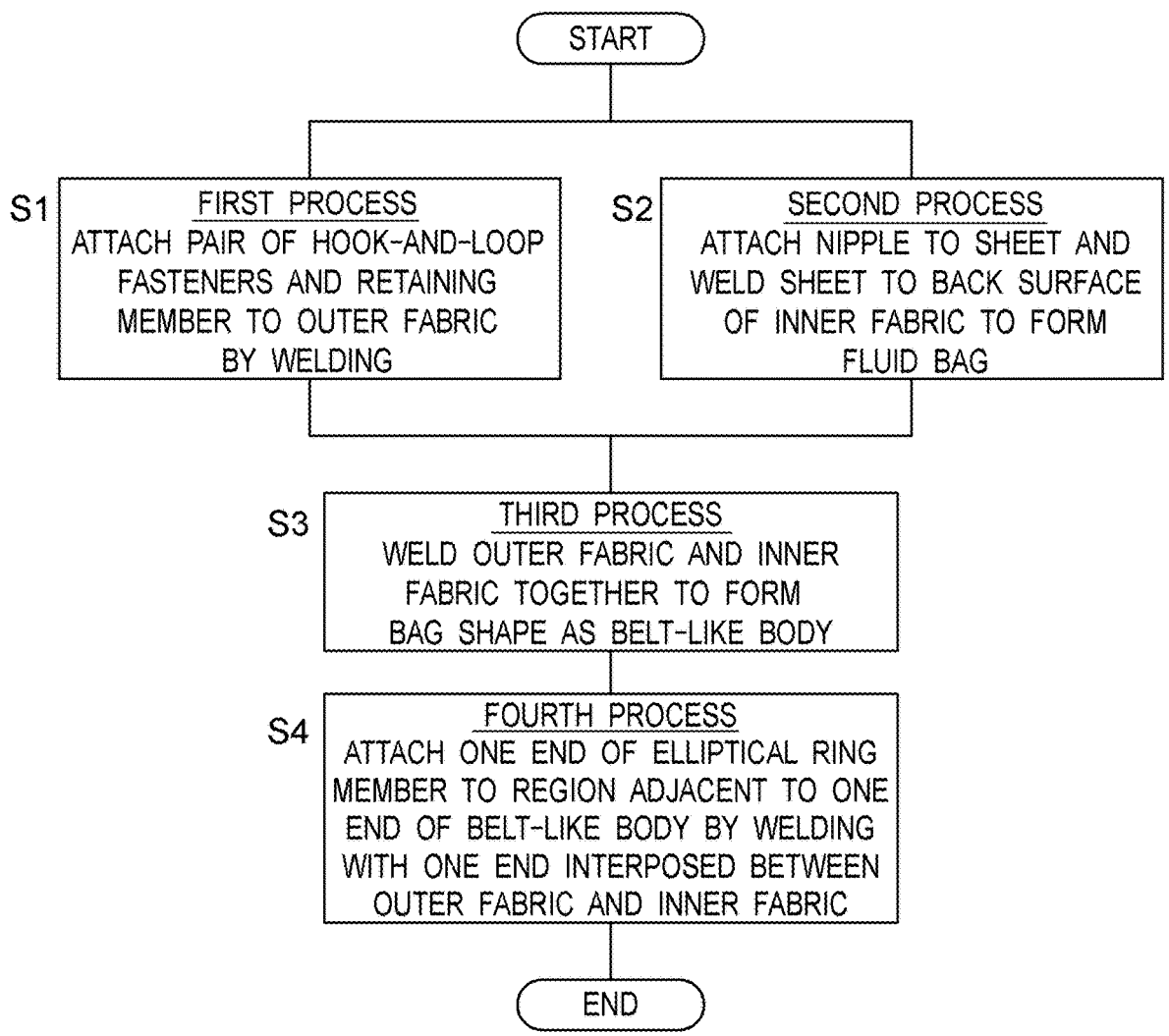

BLOOD PRESSURE MEASUREMENT CUFF AND METHOD FOR MANUFACTURING SAME

CROSS-REFERENCE TO RELATED APPLICATION

This is a continuation application of International Application No. PCT/JP2020/026780, with an International filing date of Jul. 9, 2020, which claims priority of Japanese Patent Application No. 2019-132816 filed on Jul. 18, 2019, the entire content of which is hereby incorporated by reference.

TECHNICAL FIELD

The present invention relates to a blood pressure measurement cuff, and more particularly, to a foldable blood pressure measurement cuff that is wound around a measurement part to compress the measurement part. The present invention further relates to a method for manufacturing a blood pressure measurement cuff by which such a blood pressure measurement cuff is manufactured.

BACKGROUND

Conventional examples of such a blood pressure measurement cuff include a blood pressure measurement cuff disclosed in Patent Document 1 (JP 2013-34791 A), the blood pressure measurement cuff including a belt-like body (cuff body) including an outer fabric and an inner fabric sewn together into a bag shape, the belt-like body housing an air bag (expansion bag), a ring member rotatably attached to a part near one end (proximal end) of the belt-like body in a longitudinal direction (corresponding to a circumferential direction of the measurement part), and a tube disposed in a space (storage space) between the outer fabric and the inner fabric near the other end (distal end) of the belt-like body in the longitudinal direction. This tube is made of an elastic member such as rubber. The tube can be inserted through the ring member in a pressed state and does not pass through the ring member in a natural state. A hook-like hook-and-loop fastener is attached to a region of the front surface of the outer fabric near the other end of the belt-like body in the longitudinal direction. A loop-like hook-and-loop fastener to be engaged with the hook is attached to a region of the front surface of the outer fabric between the hook-like hook-and-loop fastener and the ring member. When the blood pressure measurement cuff attaches to the left upper arm as the measurement part, a part (including the tube) contiguous with the other end of the belt-like body is inserted through the ring member with the outer fabric positioned on the outer circumferential side and the inner fabric positioned on the inner circumferential side to make the belt-like body substantially cylindrical. At this time, the tube prevents the other end (distal end) of the belt-like body from falling out of the ring member. The left upper arm is passed through the cylindrical belt-like body, and the part contiguous with the other end of the belt-like body is first pulled away from the left upper arm toward the left side of the body by the right hand and then folded back (referred to as a foldable type). Then, the hook-like hook-and-loop fastener near the other end of the belt-like body is engaged with the loop-like hook-and-loop fastener on the front surface of the opposite outer fabric (completion of attachment). During blood pressure measurement, air is supplied to the air bag from the outside of the belt-like body to compress the measurement part.

SUMMARY

In order to manufacture the above-described foldable blood pressure measurement cuff, typically, after forming the belt-like body into a bag shape by sewing, the above-described tube is inserted between the outer fabric and the inner fabric that make up the belt-like body to be enclosed in the space (storage space) near the other end (distal end) by sewing. This makes the assembly process complicated and makes automation difficult.

Further, a possible solution to reduce labor and cost is to assemble the above-described foldable blood pressure measurement cuff by, for example, welding other than sewing. In this case, when the tube is enclosed in the space (storage space) near the other end (distal end) by welding, the outer fabric and the inner fabric are relatively largely inclined around the tube with respect to the thickness direction due to the outer diameter of the tube. This makes it difficult to stack the outer fabric and the inner fabric together in the thickness direction using a welding tool and weld the outer fabric and the inner fabric together.

It is therefore an object of the present invention to provide a foldable blood pressure measurement cuff that can be easily assembled by welding. It is another object of the present invention to provide a method for manufacturing a blood pressure measurement cuff by which such a foldable blood pressure measurement cuff can be easily assembled by welding.

In order to solve the above-described problems, a blood pressure measurement cuff according to the present disclosure is a blood pressure measurement cuff that is foldable and wound around a measurement part to compress the measurement part, the blood pressure measurement cuff including a belt-like body including an outer fabric and an inner fabric facing each other to form a bag shape, the belt-like body housing a fluid bag, an elliptical ring member having one side attached, along a direction intersecting the belt-like body, to a region adjacent to one end of the belt-like body in a longitudinal direction corresponding to a circumferential direction of the measurement part, a retaining member provided to a region adjacent to an other end of the belt-like body opposite from the one end, and a fixing member provided to a front surface of the outer fabric of the belt-like body, the fixing member fixing a part contiguous with the other end of the belt-like body that is folded back through the elliptical ring member when attached to an opposite part of the outer fabric. An end opening is provided to the region adjacent to the other end of the outer fabric, and the retaining member includes a projection part that is flexible and projects, in a thickness direction, outward of the belt-like body from a back surface of the outer fabric through the end opening, and support parts, each being flat plate-like, contiguous with a base of the projection part, and welded to the back surface around the end opening of the outer fabric along the region adjacent to the other end.

Herein, the "outer fabric" and the "inner fabric" that make up the belt-like body refer to fabrics positioned on the outer circumferential side and the inner circumferential side, respectively, when the belt-like body is wound around the measurement part. The "fabric" is not limited to a knitted fabric, and may be made of one or more layers of resin. The "front surface" of the outer fabric refers to one of the surfaces of the outer fabric that is opposite from the inner fabric. A "back surface" of the outer fabric (to be described later) refers to one of the surfaces of the outer fabric that faces the inner fabric. The outer fabric and the inner fabric may make up all or part of the fluid bag.

The "longitudinal direction" of the belt-like body refers to a direction corresponding to the circumferential direction of the measurement part when attached. The "thickness direction" of the belt-like body refers to a direction orthogonal to the plane on which the belt-like body extends. The "one end" and the "other end" of the belt-like body each refer to a true end (one point) in the longitudinal direction.

According to another aspect, a method for manufacturing a blood pressure measurement cuff according to the present disclosure is a method for manufacturing the blood pressure measurement cuff, the method including a first process and a second process that are performed in parallel with each other or sequentially, the first process being performed on the outer fabric provided with the first opening, the second opening, and the end opening, the second process being performed on the inner fabric, the first process including a process of welding each of the peripheral parts of the pair hook-and-loop fasteners to a corresponding one of the back surface around the first opening of the outer fabric and the back surface around the second opening of the outer fabric to expose each of the main parts surrounded by the peripheral parts of the pair hook-and-loop fastener to the front surface of the outer fabric through a corresponding one of the first opening and the second opening, and a process of welding the support parts of the retaining member to the back surface around the end opening of the outer fabric to cause the projection part of the retaining member to project outward of the belt-like body through the end opening in the thickness direction, the second process including a process of welding a stretchable sheet to the back surface of the inner fabric with the stretchable sheet facing the back surface to form the fluid bag, a third process of welding the outer fabric and the inner fabric together with the fluid bag placed between the outer fabric and the inner fabric and the region adjacent to the one end left to form a bag shape as the belt-like body, and a fourth process of attaching, along the direction intersecting the belt-like body, the one side of the elliptical ring member to the region adjacent to the one end of the belt-like body by welding with the one end interposed between the outer fabric and the inner fabric.

The "back surface" of the inner fabric refers to one of the surfaces of the inner fabric that faces the outer fabric.

According to yet another aspect, a blood pressure measurement cuff according to the present disclosure is a foldable blood pressure measurement cuff that is wound around a measurement part to compress the measurement part, the blood pressure measurement cuff including a belt-like body including an outer fabric and an inner fabric facing each other to form a bag shape, the belt-like body housing a fluid bag, an elliptical ring member having one side attached, along a direction intersecting the belt-like body, to a region adjacent to one end of the belt-like body in a longitudinal direction corresponding to a circumferential direction of the measurement part, a retaining member provided to a region adjacent to an other end of the belt-like body opposite from the one end, and a fixing member provided to a front surface of the outer fabric of the belt-like body, the fixing member fixing a part contiguous with the other end of the belt-like body that is folded back through the elliptical ring member when attached to an opposite part of the outer fabric. An end opening is provided to the region adjacent to the other end of the outer fabric to penetrate the outer fabric and the inner fabric, and the retaining member includes a projection part that is flexible and projects, in a thickness direction, outward of the belt-like body from the inner fabric toward the outer fabric through the end opening, and support parts, each being flat plate-like, contiguous with a base of the projection part, and collectively welded to a part around the end opening of the outer fabric and the inner fabric from a side of the inner fabric along the region adjacent to the other end.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 5 is a diagram illustrating a flow of a method for manufacturing the blood pressure measurement cuff.

DETAILED DESCRIPTION

Hereinafter, embodiments of the present invention will be described in detail with reference to the drawings.

(Structure of Blood Pressure Measurement Cuff)

Figure 1:
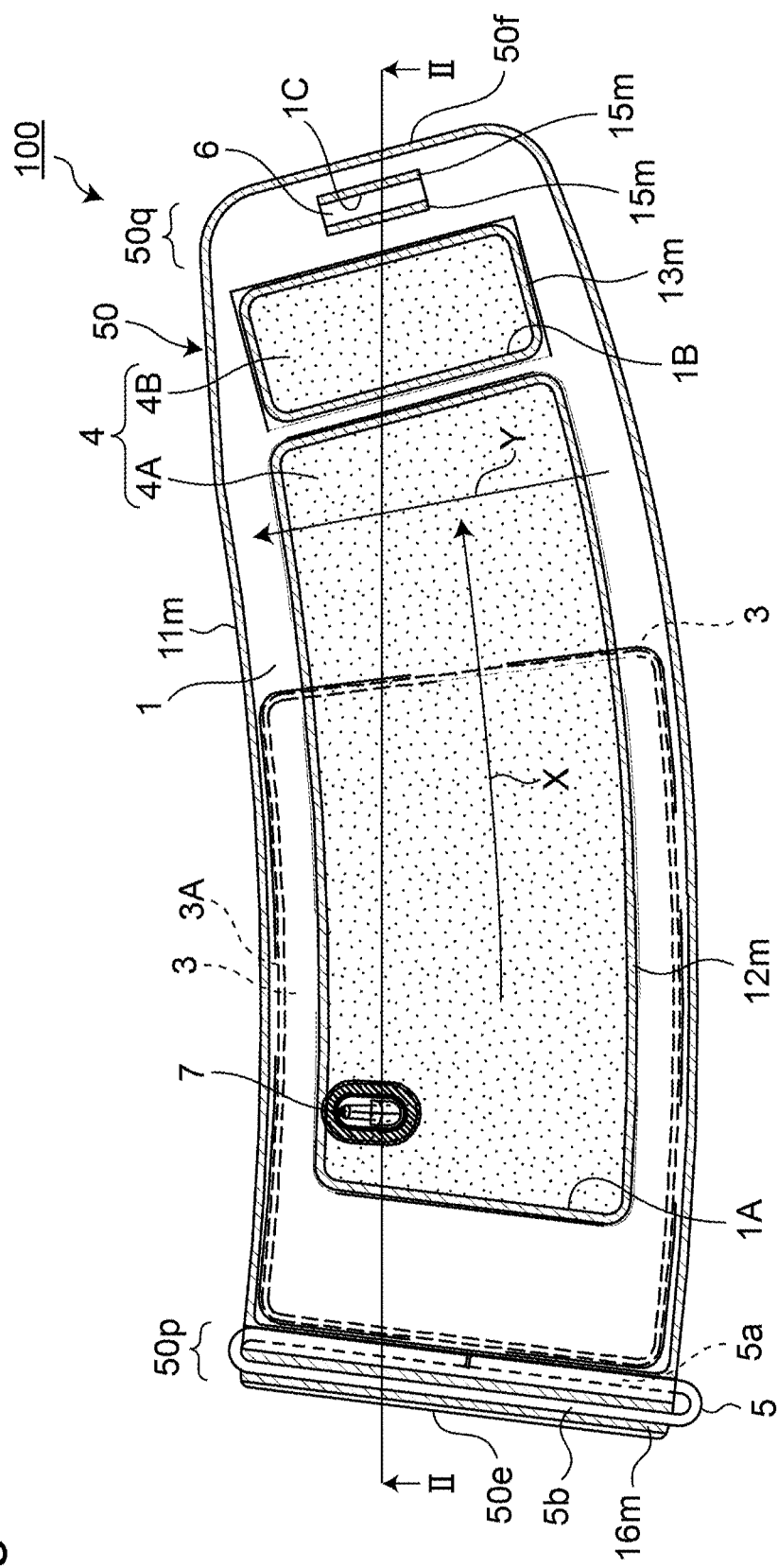
FIG. 1 is a plan view of a blood pressure measurement cuff according to an embodiment of the present invention, as viewed from an outer fabric side in an unfolded state.
Figure 2:
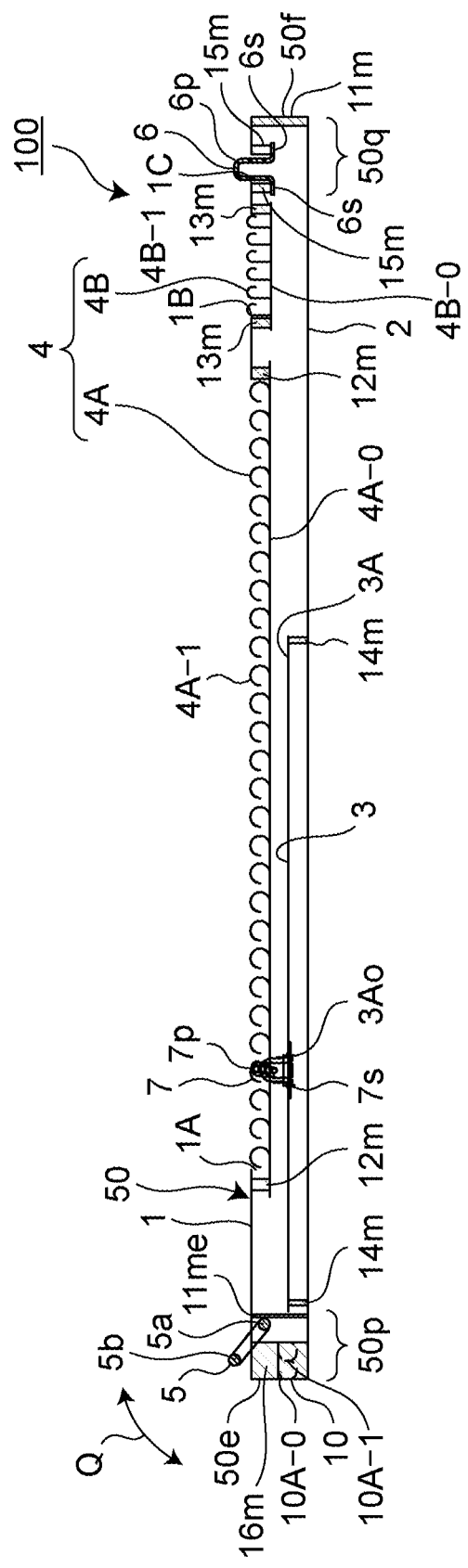
FIG. 2 is a cross-sectional view of the blood pressure measurement cuff illustrated in FIG. 1, taken along a line II-II.
Figure 3:
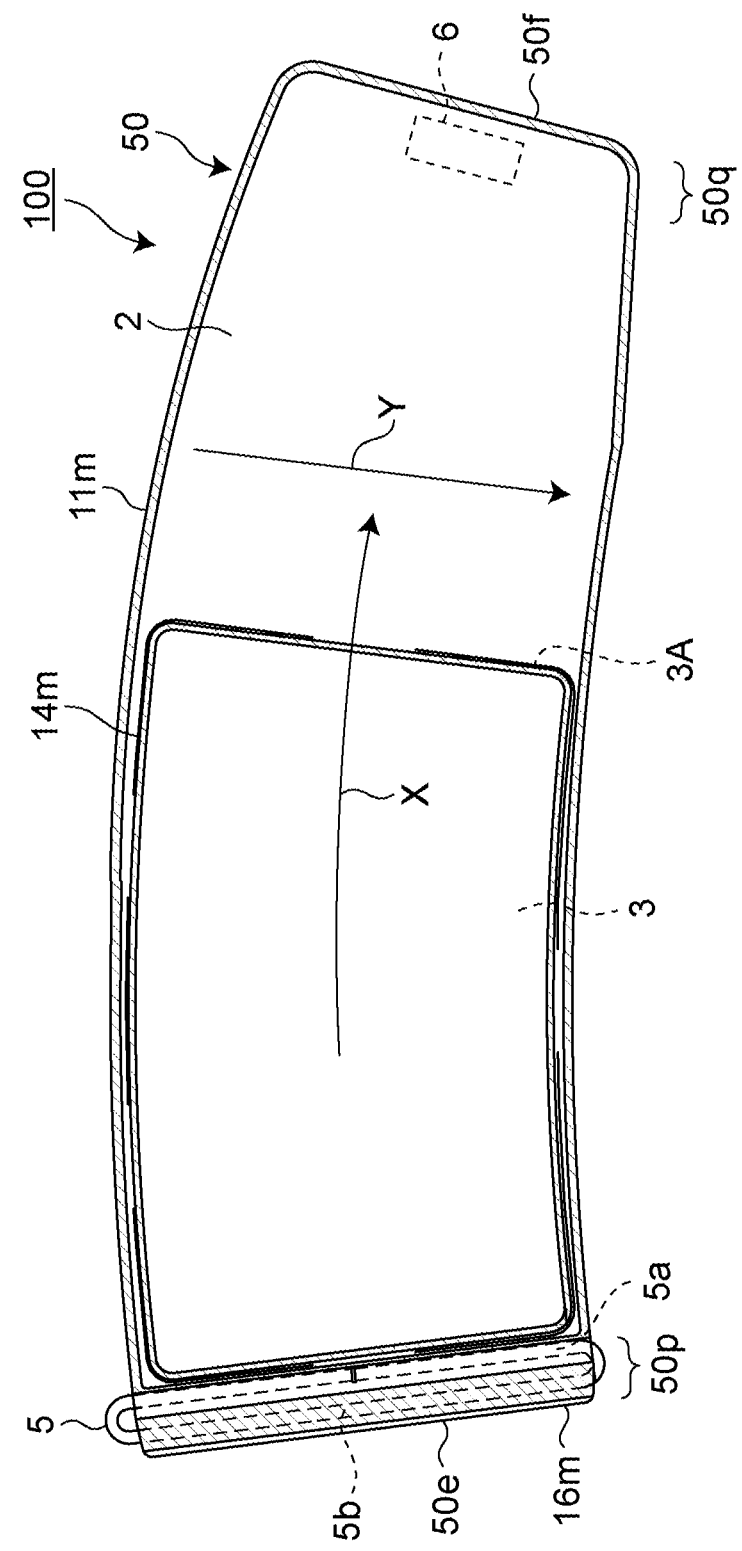
FIG. 3 is a plan view of the blood pressure measurement cuff illustrated in FIG. 1, as viewed from an inner fabric side.

FIG. 1 is a plan view of a blood pressure measurement cuff 100 according to the present embodiment, as viewed from an outer fabric 1 side. Further, FIG. 2 is a cross-sectional view of the blood pressure measurement cuff 100, taken along a line II-II in FIG. 1. Further, FIG. 3 is a plan view of the blood pressure measurement cuff 100, as viewed from an inner fabric 2 side. FIGS. 1, 2, and 3 illustrate an overall structure of the blood pressure measurement cuff 100 in an unfolded state (that is, a state where the blood pressure measurement cuff 100 is not wound around a measurement part).

As with the blood pressure measurement cuff disclosed in Patent Document 1 (JP 2013-34791 A), the blood pressure measurement cuff 100 is a foldable cuff that is wound around the measurement part to compress the measurement part. The blood pressure measurement cuff 100 is wound around the measurement part (for example, a left upper arm) along a circumferential direction. The circumferential direction of the measurement part corresponds to a "longitudinal direction X" of the blood pressure measurement cuff 100 (in other words, a belt-like body 50 to be described later). In the plane of FIGS. 1 and 3, a direction orthogonal to the longitudinal direction X is referred to as a "width direction Y". A direction orthogonal to both the longitudinal direction X and the width direction Y is referred to as a "thickness direction Z" (see FIG. 2).

The blood pressure measurement cuff 100 includes the belt-like body 50, a fluid bag 3, a pair of hook-and-loop fasteners 4A, 4B serving as a fixing member 4, a ring member 5, a retaining member 6, and a reinforcing layer 10 (see FIG. 2).

The belt-like body 50 has an arc shape in a plan view as illustrated in FIGS. 1 and 3, and extends along the longitudinal direction X. The belt-like body 50 includes the outer fabric 1 and the inner fabric 2. The outer fabric 1 and the inner fabric 2 are welded together to form the belt-like body 50 having a bag shape. The belt-like body 50 houses the fluid bag 3 (see FIG. 2). In FIGS. 1 and 3, the outline of the fluid bag 3 is represented by a dashed line.

The outer fabric 1 that is a part of the belt-like body 50 is a fabric positioned on an outer circumferential side when the belt-like body 50 is wound around the measurement part (for example, the left upper arm). On the other hand, the inner fabric 2 that is a part of the band-shaped body 50 is a fabric positioned on an inner circumferential side when the belt-like body 50 is wound around the measurement part. Herein, the "fabric" is not limited to a knitted fabric and may be made of one or more layers of resin.

During blood pressure measurement, the inner fabric 2 is in contact with the measurement part. The outer fabric 1 is located opposite from the inner fabric 2 and does not come into contact with the measurement part during blood pressure measurement. The outer fabric 1 and the inner fabric 2 have their respective parts near peripheries welded along a ring line (which may be regarded as a welded region) 11m. As described above, the welding results in the formation of belt-like body 50 in a bag shape (the welded line 11m is represented by diagonal lines).

Note that, in a state where the outer fabric 1 and the inner fabric 2 are welded together, a surface of the outer fabric 1 and a surface of the inner fabric 2, both facing outward of the belt-like body 50, are referred to as a "front surface" of the outer fabric 1 and a "front surface" of the inner fabric 2, respectively. A surface of the outer fabric 1 facing the inner fabric 2 is referred to as a "back surface" of the outer fabric 1. A surface of the inner fabric 2 facing the outer fabric 1 is referred to as a "back surface" of the inner fabric 2. During blood pressure measurement, the front surface of the inner fabric 2 comes into contact with the measurement part.

In this example, the inner fabric 2 is made of a laminate of two layers including a polyester fabric and a stretchable polyurethane film. The polyester fabric serves as the front surface of the inner fabric 2, and the polyurethane film serves as the back surface of the inner fabric 2. Further, the outer fabric 1 is made of a laminate of three layers including a nylon fabric, a tarpaulin layer, and a stretchable polyurethane film. The nylon fabric serves as the front surface of the outer fabric 1, and the polyurethane film serves as the back surface of the outer fabric 1.

The belt-like body 50 has two ends (one end 50e and another end 50f) in the longitudinal direction X. The other end 50f is located opposite from the one end 50e in the longitudinal direction X. In the longitudinal direction X, one side 5a of the ring member 5 is attached to a region 50p of the belt-like body 50 adjacent to the one end 50e. The one side 5a of the ring member 5 is disposed on the belt-like body 50 along the width direction Y intersecting the longitudinal direction X. The one end 50e and the other end 50f each refer to a true end (one point) in the longitudinal direction X.

The ring member 5 is made of, for example, a metal material and has an elliptical shape (including two rod-like sides 5a, 5b and two arc-like connecting parts connecting ends of the sides 5a, 5b). In the example illustrated in FIG. 2, the one side 5a of the ring member 5 is disposed (interposed) between the outer fabric 1 and the inner fabric 2 in the region 50p of the belt-like body 50. The other side 5b is disposed outside the outer fabric 1. As described above, with the one side 5a of the ring member 5 interposed between the outer fabric 1 and the inner fabric 2, the ring member 5 is rotatable about the one side 5a relative to the belt-like body 50 as indicated by an arrow Q.

The above-described welded line 11m passes through a region (welded region 11me illustrated in FIG. 2) located away from the one end 50e of the belt-like body 50 by the size of the region 50p (8 to 13 mm) in the +X direction. The welded region 11me and a welded region 16m to be described later regulate the movement of the one side 5a of the ring member 5 in the belt-like body 50 in the longitudinal direction X.

As illustrated in FIGS. 1 and 2, an end opening 1C having a substantially rectangular shape is provided to a region 50q of the outer fabric 1 adjacent to the other end 50f in the longitudinal direction X, and the retaining member 6 is disposed to project from the end opening 1C.

Figure 4A:
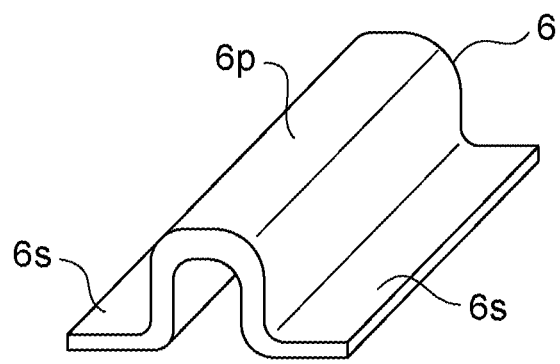
FIG. 4A is an enlarged perspective view of a retaining member alone that is a component of the blood pressure measurement cuff.
Figure 4B:
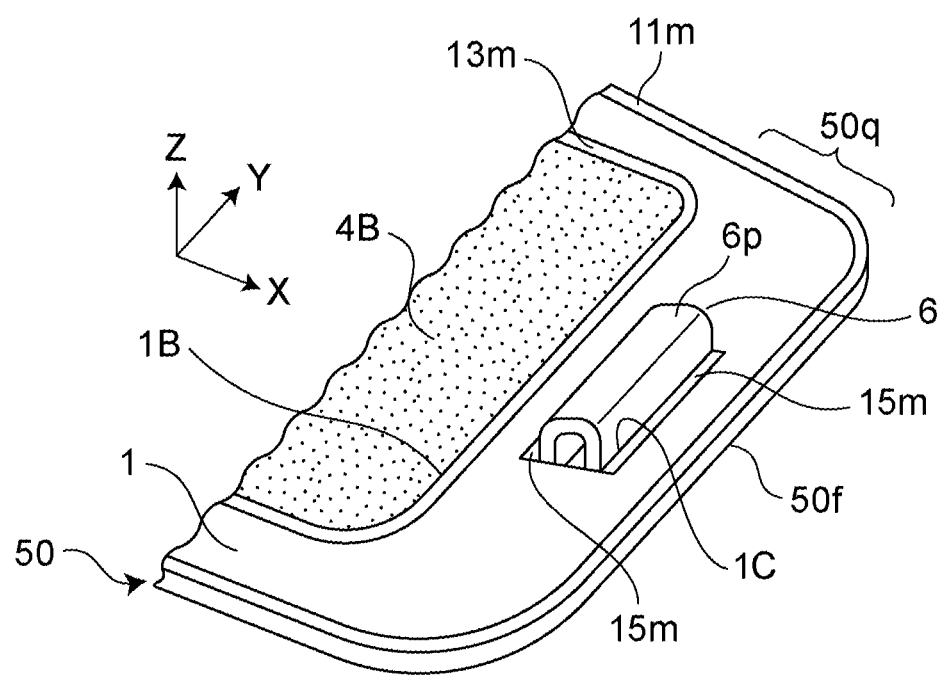
FIG. 4B is a perspective view of a region where the retaining member of the blood pressure measurement cuff is provided.

FIG. 4A is an enlarged view of only the retaining member 6, and FIG. 4B illustrates a region including and around the region 50q of the belt-like body 50 where the retaining member 6 is provided. In this example, the retaining member 6 is made of a single-piece material having flexibility (for example, an elastomer), and has a projection part 6p projecting outward of the belt-like body 50 through the end opening 1C in the thickness direction Z, and flat plate-like support parts 6s, 6s connected to a base of the projection part 6p. A cross section of the projection part 6p of the retaining member 6 in the longitudinal direction X has an inverted U shape with a rounded distal end in the thickness direction Z. The support parts 6s, 6s are welded to the back surface of the outer fabric 1 along straight lines 15m, 15m (see FIGS. 1 and 2). In this example, the projection part 6p has a length of about 7.5 mm in the X-direction. The retaining member 6 has a length of about 15 mm in the X direction. Further, the projection part 6p (and the support parts 6s) has a length of about 35 mm in the Y direction. A length in the Z direction (thickness) from the front surface of the inner fabric 2 to the distal end of the projection part 6p is about 8 mm in this example, and is set larger than a gap between the sides 5a, 5b of the ring member 5 (about 7 mm in this example).

In order to attach the blood pressure measurement cuff 100 to the measurement part (for example, a left upper arm 90), when a part (including the retaining member 6) contiguous with the other end 50f of the belt-like body 50 is inserted through the ring member 5 to make the belt-like body 50 substantially cylindrical, the retaining member 6 prevents the other end 50f of the belt-like body 50 from falling out of the ring member 5 (details will be described later).

As illustrated in FIGS. 1 and 2, a first opening 1A is provided to a center region of the outer fabric 1 in the longitudinal direction X, and a second opening 1B is provided to a region between the first opening 1A and the end opening 1C. The loop-like hook-and-loop fastener 4A and the hook-like hook-and-loop fastener 4B are provided to occupy the openings 1A, 1B, respectively. The hook-and-loop fastener 4A includes a flat base layer 4A-0 and a large number of loops 4A-1 provided to stand on the base layer 4A-0. The hook-and-loop fastener 4B includes a flat base layer 4B-0 and a large number of hooks 4B-1 provided to stand on the base layer 4B-0.

A peripheral part 4As of the loop-like hook-and-loop fastener 4A is welded to the back surface around the first opening 1A of the outer fabric 1 along a ring line 12m. Further, a peripheral part 4Bs of the hook-like hook-andloop fastener 4B is welded to the back surface around the second opening 1B of the outer fabric 1 along a ring line 13m. This causes a main parts 4Ai, 4Bi of the pair of hook-and-loop fasteners 4A, 4B (parts surrounded by the peripheral parts 4As, 4Bs) to be exposed to the front surface of the outer fabric 1 through the first opening 1A and the second opening 1B, respectively. Note that the peripheral parts 4As, 4Bs have neither a loop nor a hook so as to be flat.

When attached, the hook-like hook-and-loop fastener 4B is folded back through the ring member 5 continuously with the other end 50f of the belt-like body 50 and is detachably engaged with the loop-like hook-and-loop fastener 4A occupying the opposite part of the outer fabric 1.

As illustrated in FIGS. 2 and 3, in this example, the fluid bag 3 is made of the inner fabric 2 and a sheet (made of a stretchable polyurethane film) 3A facing the back surface of the inner fabric 2 that are welded together along a ring line 14m.

A nipple 7 is attached to a part of the sheet 3A. Further, the outer fabric 1 (more specifically, the main part 4Ai of the hook-and-loop fastener 4A provided along the outer fabric 1) has an opening 4An (illustrated in, for example, FIGS. 7A and 7B to be described later) provided for exposing the nipple 7. The nipple 7 includes a cylindrical part 7p projecting outward of the belt-like body 50 through the opening 4An, and a flange-like support part 7s contiguous with a base of the cylindrical part 7p. The support part 7s is welded to the sheet 3A, thereby causing the sheet 3A to support the nipple 7. A through hole 3Ao is provided to a region of the sheet 3A where the nipple 7 is provided. This allows a fluid to flow through the sheet 3A (and the main part 4Ai of the hook-and-loop fastener 4A). That is, it is possible to supply the fluid to the fluid bag 3 from the outside of the belt-like body 50 through the nipple 7. Conversely, it is possible to discharge the fluid from the fluid bag 3 to the outside of the belt-like body 50 through the nipple 7.

As illustrated in FIG. 2, of the region 50p adjacent to the one end 50e of the belt-like body 50, a region between the one end 50e and the one side 5a of the ring member 5 is welded as the welded region 16m with the reinforcing layer 10 interposed between the outer fabric 1 and the inner fabric 2. The reinforcing layer 10 is a layer higher in bending resistance than the inner fabric 2 and the outer fabric 1. Bending resistance can be measured, for example, by the 45° cantilever method. In this example, the reinforcing layer 10 is made of the same material as the loop-like hook-and-loop fastener 4A for commonality of members and includes a flat base layer 10A-0 and a large number of loops 10A-1 provided to stand on the base layer 10A-0. This allows commonality of materials between the hook-and-loop fastener 4A and the reinforcing layer 10 and thus allows a reduction in manufacturing cost. Further, when the blood pressure measurement cuff 100 is attached to the measurement part, the reinforcing layer 10 can prevent the region 50p adjacent to the one end 50e of the belt-like body 50 from being bent and caught by the measurement part, that is, the skin.

(Method for Manufacturing Blood Pressure Measurement Cuff)

Next, an example of a method for manufacturing the blood pressure measurement cuff 100 will be described with reference to the flowchart of FIG. 5.

Figure 6A:
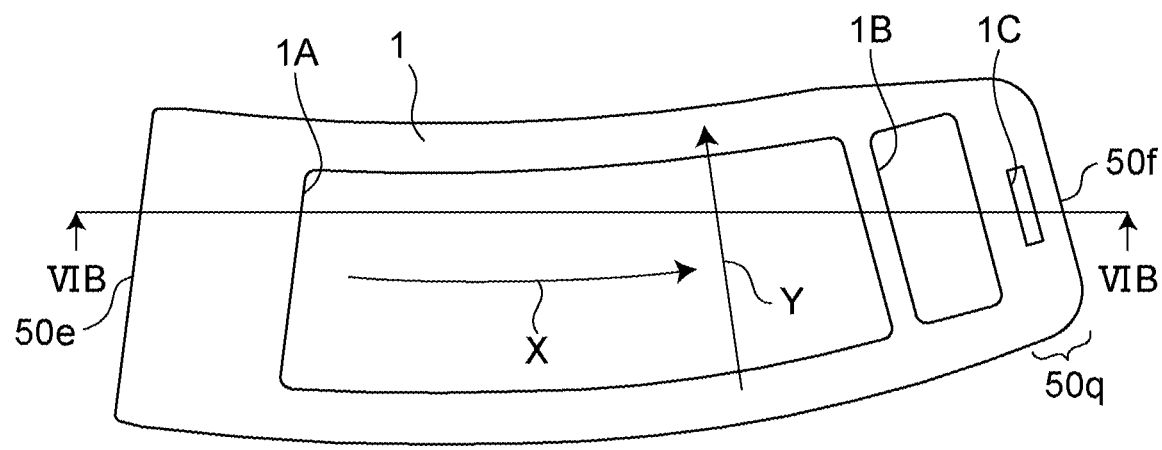
FIG. 6A is a plan view of the outer fabric prepared for manufacturing the blood pressure measurement cuff.
Figure 6B:
FIG. 6B is a cross-sectional view (end view) taken along a line VIB-VIB in FIG. 6A.

First, in step S1 of FIG. 5, a process (first process) on the outer fabric 1 is performed. Here, as illustrated in FIGS. 6A and 6B, the outer fabric 1 is already cut into the shape of the outer fabric 1 illustrated in FIG. 1, and in particular, the first opening 1A, the second opening 1B, and the end opening 1C are already provided. Note that FIG. 6A illustrates the outer fabric 1 as viewed from the front surface side (the same applies to FIGS. 7A, 8A, . . . , and 12A to be described later). FIG. 6B is a cross-sectional view (end view) taken along a line VIB-VIB in FIG. 6A (the same applies to FIGS. 7B, 8B, . . . , and 12B with respect to FIGS. 7A, 8A, and . . . , and 12A to be described later).

Figure 7A:
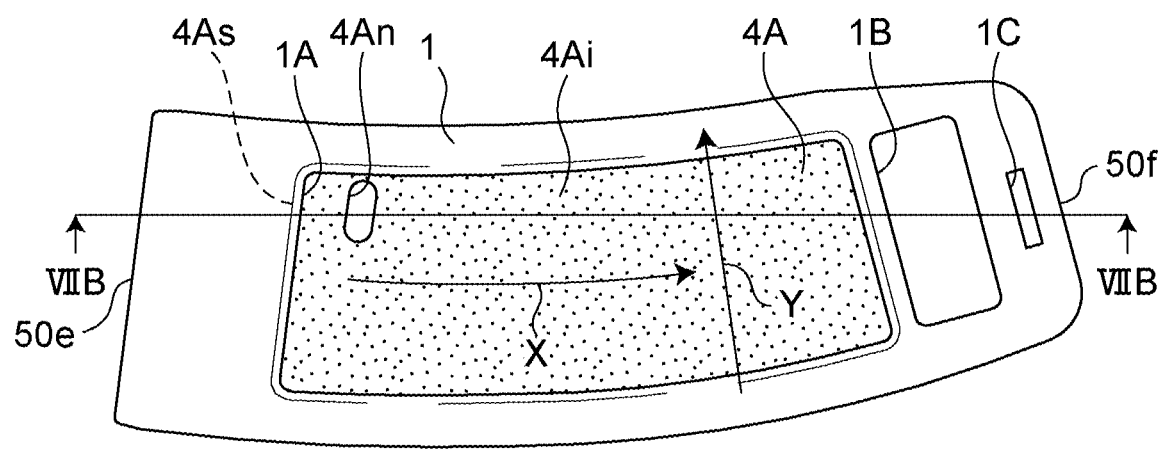
FIG. 7A is a plan view of the blood pressure measurement cuff, as viewed from a front surface side of the outer fabric, for describing a process of welding a loop-like hook-and-loop fastener to the outer fabric, the process belonging to a first process of the method for manufacturing the blood pressure measurement cuff.
Figure 7B:
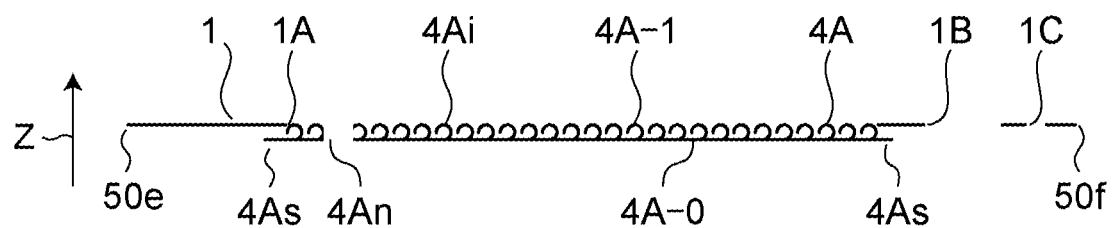
FIG. 7B is a cross-sectional view taken along a line VIIB-VIIB in FIG. 7A.
Figure 8A:
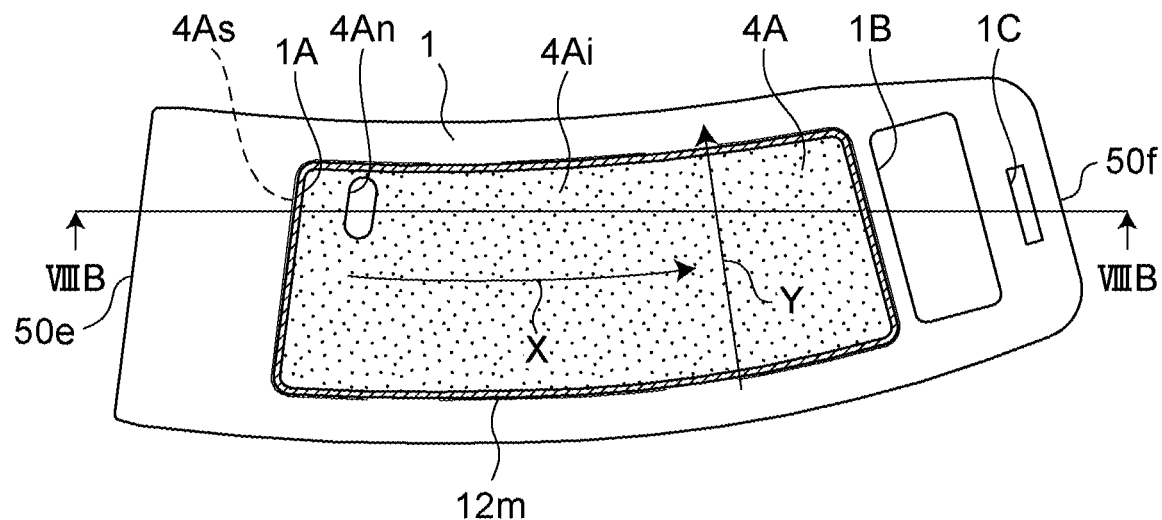
FIG. 8A is a plan view of the blood pressure measurement cuff, as viewed from the front surface side of the outer fabric, for describing the process of welding the loop-like hook-and-loop fastener to the outer fabric, the process belonging to the first process of the method for manufacturing the blood pressure measurement cuff.
Figure 8B:
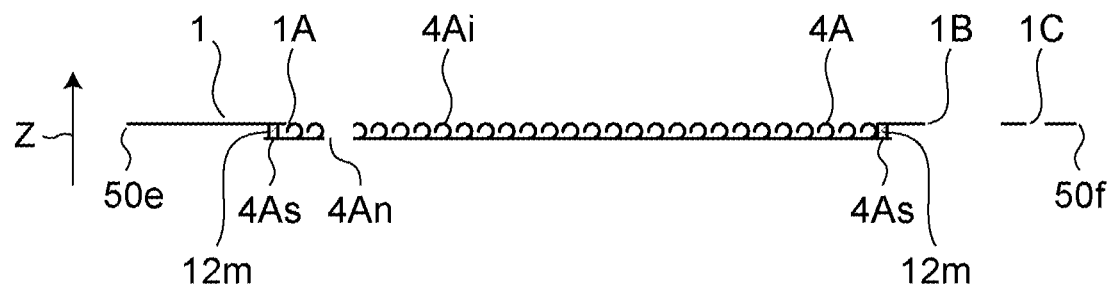
FIG. 8B is a cross-sectional view taken along a line VIIIB-VIIIB in FIG. 8A.
Figure 9A:
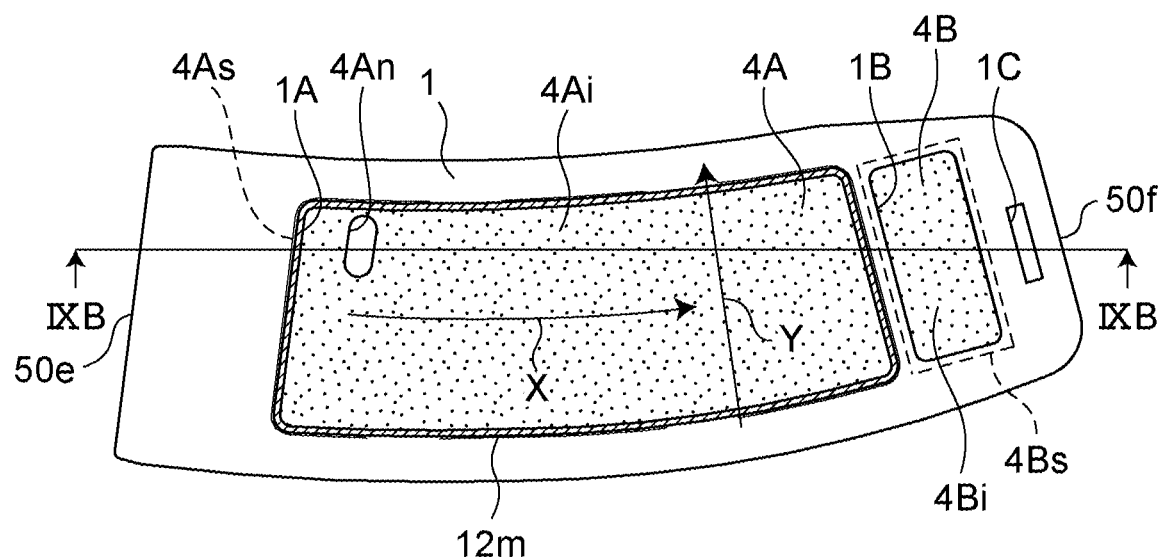
FIG. 9A is a plan view of the blood pressure measurement cuff, as viewed from the front surface side of the outer fabric, for describing a process of welding a hook-like hook-and-loop fastener to the outer fabric, the process belonging to the first process of the method for manufacturing the blood pressure measurement cuff.
Figure 9B:
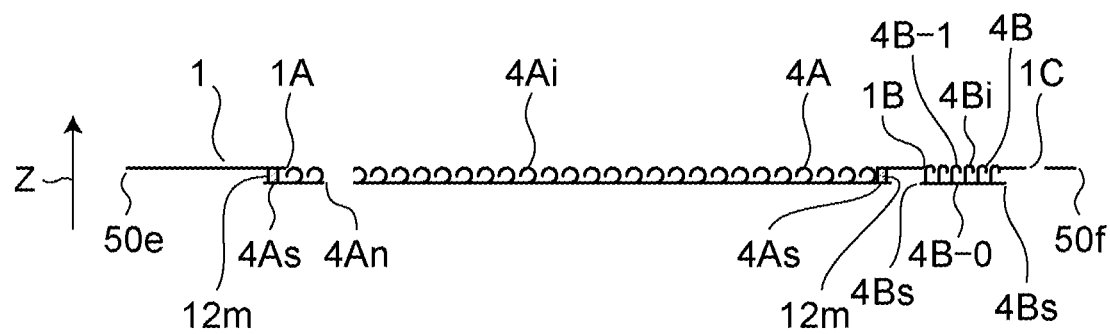
FIG. 9B is a cross-sectional view taken along a line IXB-IXB in FIG. 9A.
Figure 10A:
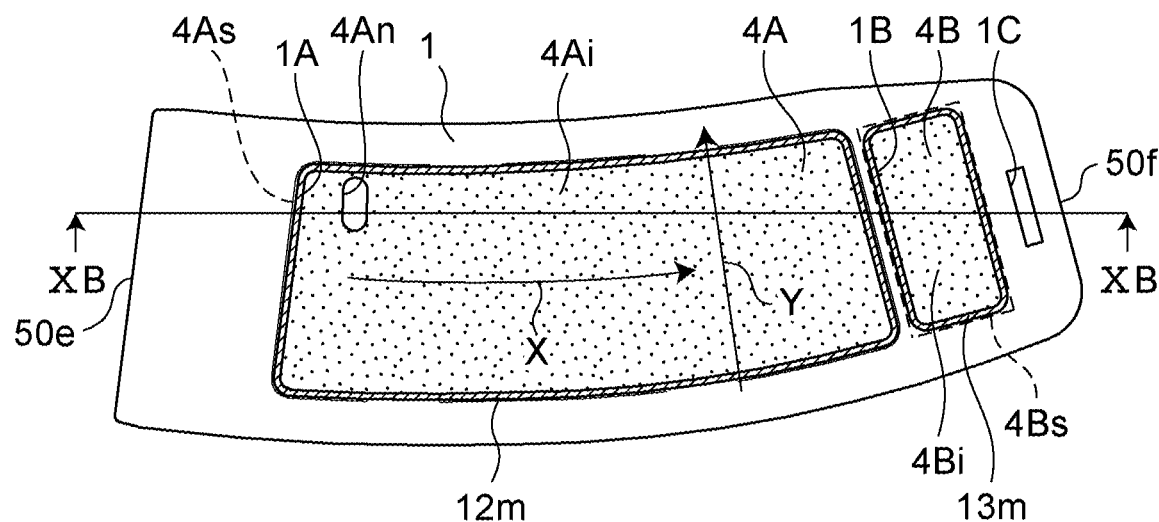
FIG. 10A is a plan view of the blood pressure measurement cuff, as viewed from the front surface side of the outer fabric, for describing the process of welding the hook-like hook-and-loop fastener to the outer fabric, the process belonging to the first process of the method for manufacturing the blood pressure measurement cuff.
Figure 10B:
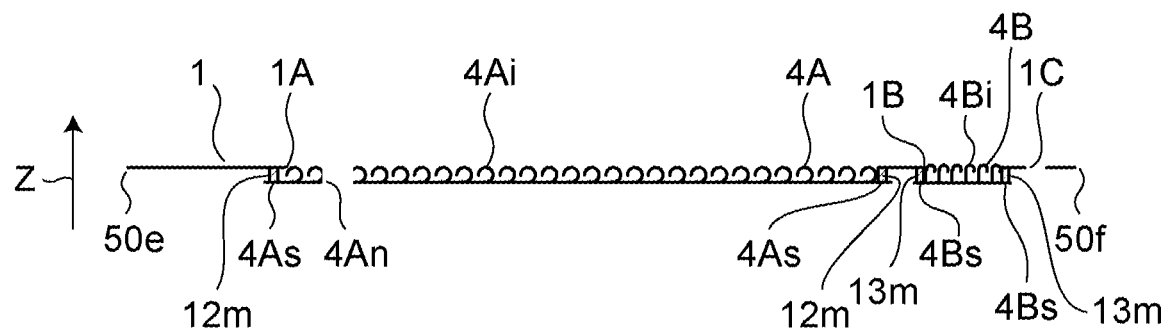
FIG. 10B is a cross-sectional view taken along a line XB-XB in FIG. 10A.
Figure 11A:
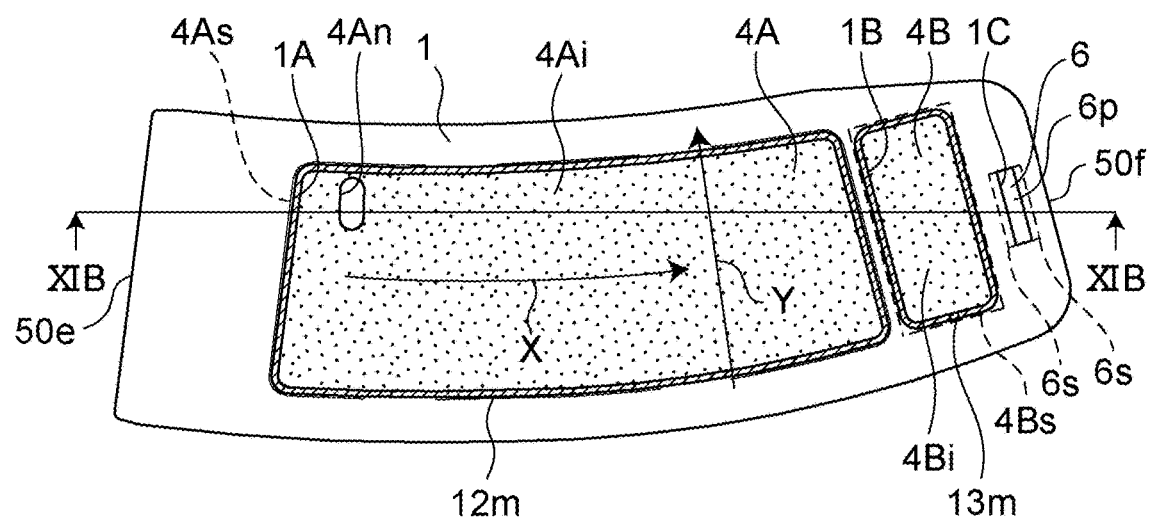
FIG. 11A is a plan view of the blood pressure measurement cuff, as viewed from the front surface side of the outer fabric, for describing a process of welding a retaining member to the outer fabric, the process belonging to the first process of the method for manufacturing the blood pressure measurement cuff.
Figure 11B:
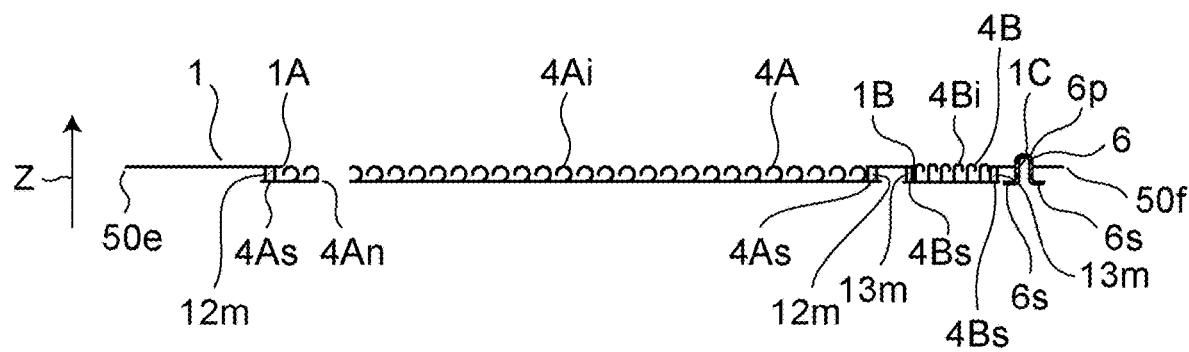
FIG. 11B is a cross-sectional view taken along a line XIB-XIB in FIG. 11A.
Figure 12A:
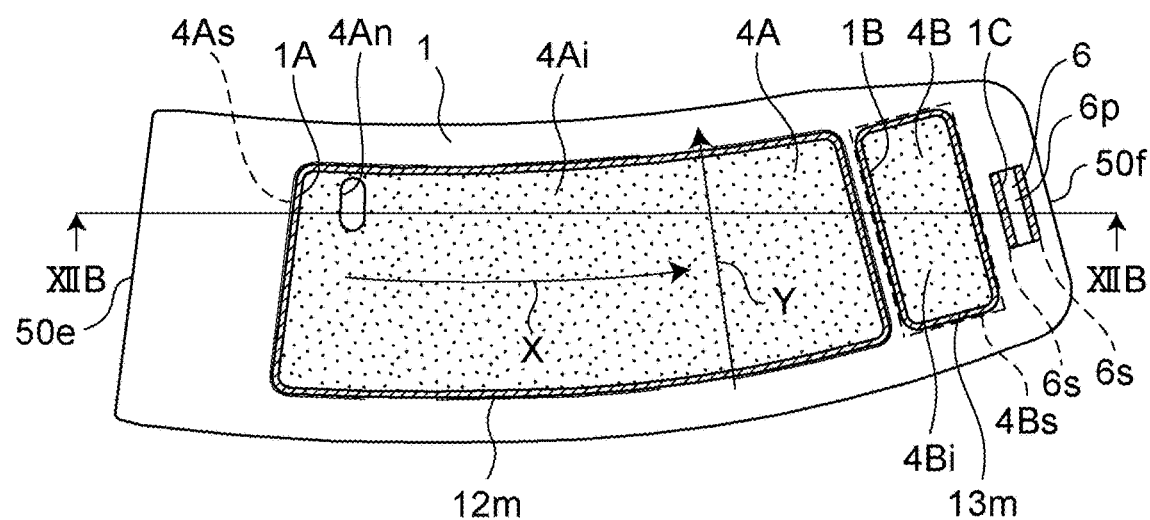
FIG. 12A is a plan view of the blood pressure measurement cuff, as viewed from the front surface side of the outer fabric, for describing the process of welding the retaining member to the outer fabric, the process belonging to the first process of the method for manufacturing the blood pressure measurement cuff.
Figure 12B:
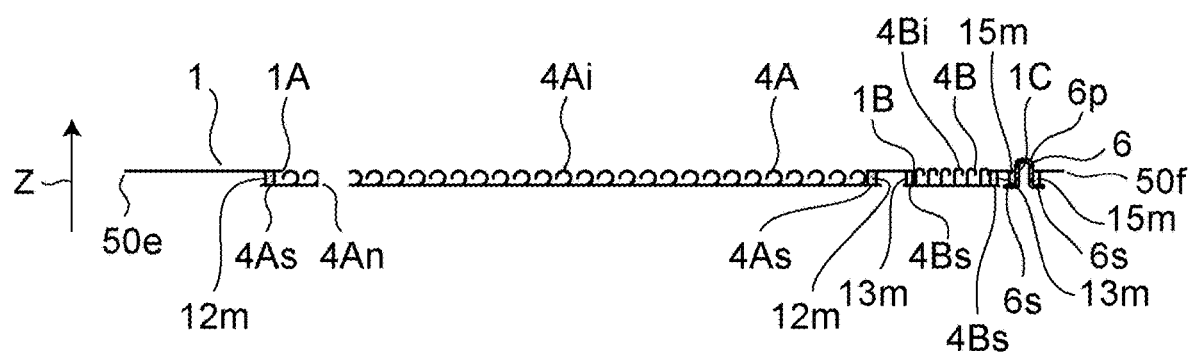
FIG. 12B is a cross-sectional view taken along a line XIIB-XIIB in FIG. 12A.

In step S1 of FIG. 5 (first process), first, as illustrated in FIGS. 7A and 7B, the loop-like hook-and-loop fastener 4A is aligned with the first opening 1A of the outer fabric 1. Specifically, the peripheral part 4As of the hook-and-loop fastener 4A is placed on the back surface around the first opening 1A of the outer fabric 1 in the thickness direction Z (from a side in the −Z direction) to cause the main part 4Ai of the hook-and-loop fastener 4A to be exposed to the front surface of the outer fabric 1 through the first opening 1A. In this state, as illustrated in FIGS. 8A and 8B, the peripheral part 4As of the hook-and-loop fastener 4A is welded, using a welding tool (not illustrated), to the back surface around the first opening 1A of the outer fabric 1 along the ring line 12m. As a result, the hook-and-loop fastener 4A is attached to the outer fabric 1. Note that it is assumed that the hook-and-loop fastener 4A already has the opening 4An provided for exposing the nipple 7. Subsequently, as illustrated in FIGS. 9A and 9B, the hook-like hook-and-loop fastener 4B is aligned with the second opening 1B of the outer fabric 1. Specifically, the peripheral part 4Bs of the hook-and-loop fastener 4B is placed on the back surface around the second opening 1B of the outer fabric 1 in the thickness direction Z (from the side in the −Z direction) to cause the main part 4Bi of the hook-and-loop fastener 4B to be exposed to the front surface side of the outer fabric 1 through the second opening 1B. In this state, as illustrated in FIGS. 10A and 10B, the peripheral part 4Bs of the hook-and-loop fastener 4B is welded, using the welding tool (not illustrated), to the back surface around the second opening 1B of the outer fabric 1 along the ring line 13m. As a result, the hook-and-loop fastener 4B is attached to the outer fabric 1. Subsequently, as illustrated in FIGS. 11A and 11B, the retaining member 6 is aligned with the end opening 1C of the outer fabric 1. Specifically, the support parts 6s, 6s of the retaining member 6 are placed on the back surface, on both the sides in the X direction of the end opening 1C, of the outer fabric 1 in the thickness direction Z (from the side in the −Z direction) to cause the projection part 6p of the retaining member 6 to project outward of the belt-like body 50 through the end opening 1C in the thickness direction Z. In this state, as illustrated in FIGS. 12A and 12B, the support parts 6s, 6s of the retaining member 6 are welded, using the welding tool (not illustrated), to the back surface, on both the sides of the end opening 1C in the X direction, of the outer fabric 1 along the straight lines 15m, 15m. As a result, the retaining member 6 is attached to the region 50q adjacent to the other end 50f of the outer fabric 1.

In the above-described first process, the process of attaching the pair of hook-and-loop fasteners 4A, 4B to the outer fabric 1 is simplified (suitable for automation) because the process is performed in the thickness direction Z. Further, since the pair of hook-and-loop fasteners 4A, 4B have a planar shape, when the peripheral parts 4As, 4Bs of the pair of hook-and-loop fasteners 4A, 4B are placed on the back surface around the first opening 1A and the back surface around the second opening 1B of the outer fabric 1, respectively, the inclination of the outer fabric 1 with respect to the thickness direction Z becomes gentle. Therefore, the peripheral parts 4As, 4Bs of the pair of hook-and-loop fasteners 4A, 4B are easily welded to the back surface around the first opening 1A and the back surface around the second opening 1B of the outer fabric 1, respectively.

Likewise, in the above-described first process, the process of attaching the retaining member 6 to the outer fabric 1 is simplified (suitable for automation) because the process is performed in the thickness direction Z. Further, since the support parts 6s, 6s of the retaining member 6 have a flat plate shape, when the support parts 6s, 6s of the retaining member 6 are placed on the back surface around the end opening 1C of the outer fabric 1, the inclination of the outer fabric 1 with respect to the thickness direction Z becomes gentle. Therefore, the support parts 6s, 6s of the retaining member 6 are easily welded to the back surface around the end opening 1C of the outer fabric 1. As a result, the support parts 6s, 6s of the retaining member 6 can be easily attached to the back surface around the end opening 1C of the outer fabric 1.

Note that, in the above-described first process, the loop-like hook-and-loop fastener 4A, the hook-like hook-and-loop fastener 4B, and the retaining member 6 are attached to the outer fabric 1 in this order, but the present invention is not limited to such an order. The attachment (welding) of such three members 4A, 4B, 6 may be made in any order, or may be made in parallel with each other.

Figure 13A:
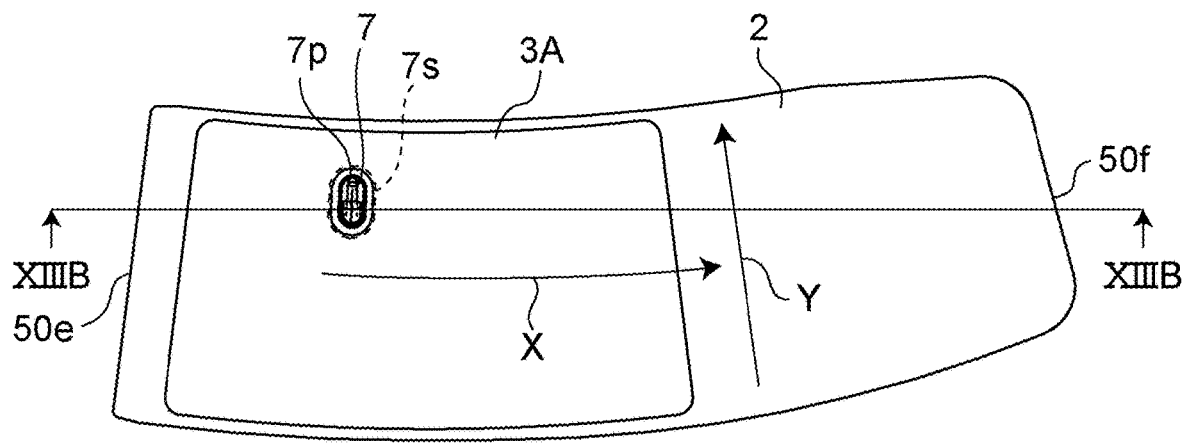
FIG. 13A is a plan view of the blood pressure measurement cuff, as viewed from a back surface side of the inner fabric, for describing a process of attaching, to the back surface of the inner fabric, a nipple and a sheet serving as a fluid bag by welding, the process belonging to a second process of the method for manufacturing the blood pressure measurement cuff.
Figure 13B:
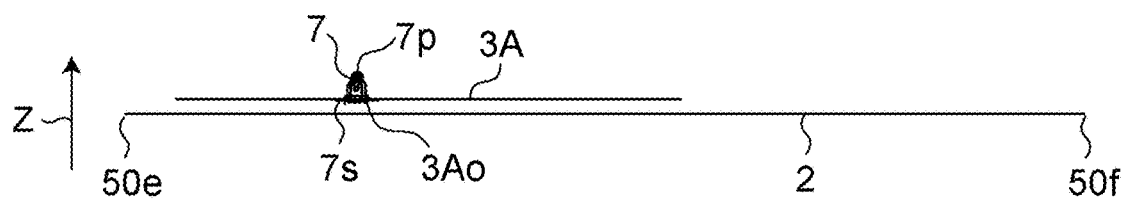
FIG. 13B is a cross-sectional view taken along a line XIIIB-XIIIB in FIG. 13A.
Figure 13C:
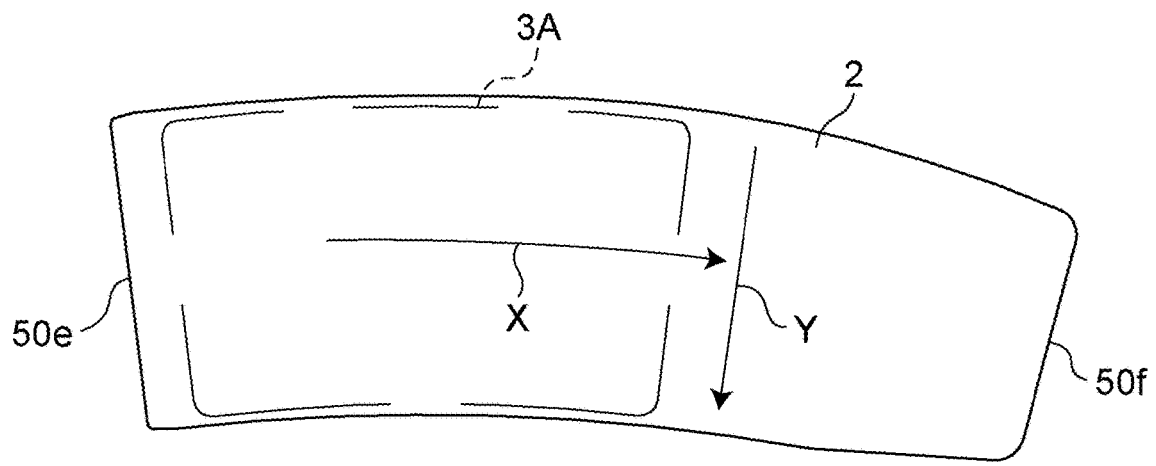
FIG. 13C is a plan view of the blood pressure measurement cuff illustrated in FIG. 13A, as viewed from a front surface side of the inner fabric.

Next, in step S2 of FIG. 5, a process (second process) on the inner fabric 2 is performed. Here, as illustrated in FIGS. 13A, 13B, and 13C, the inner fabric 2 and the sheet 3A are already cut into the shape of the inner fabric 2 and the shape of the sheet 3A illustrated in FIG. 3, respectively. Note that FIG. 13A illustrates the inner fabric 2 as viewed from the back surface side (the same applies to FIGS. 14A and 15A to be described later). FIG. 13B is a cross-sectional view (end view) taken along a line XIIIB-XIIIB in FIG. 13A (the same applies to FIGS. 14B and 15B with respect to FIGS. 14A and 15A to be described later). Note that FIG. 13C illustrates the inner fabric 2 as viewed from the front surface side (the same applies to FIGS. 14C and 15C to be described later).

Figure 14A:
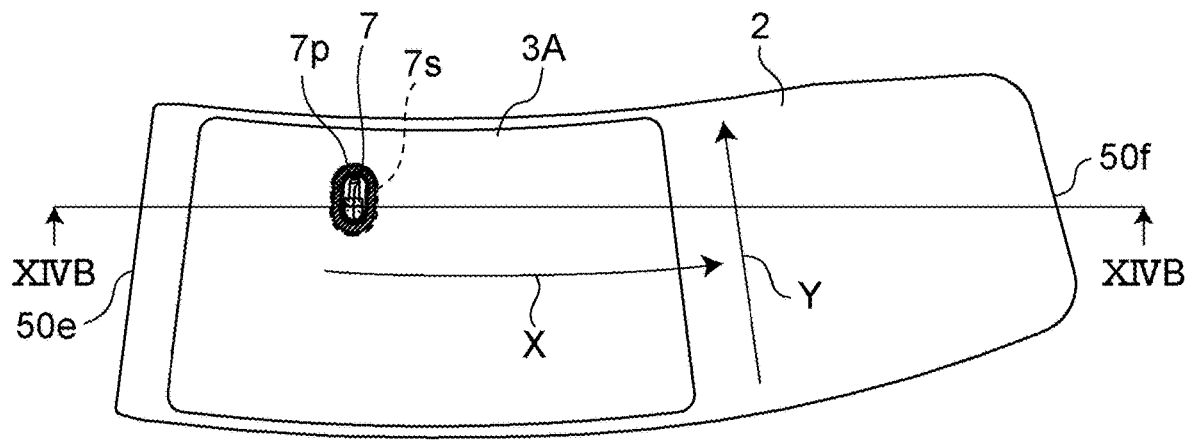
FIG. 14A is a plan view of the blood pressure measurement cuff, as viewed from the back surface side of the inner fabric, for describing the process of attaching, to the back surface of the inner fabric, the nipple and the sheet serving as the fluid bag by welding, the process belonging to the second process of the method for manufacturing the blood pressure measurement cuff.
Figure 14B:
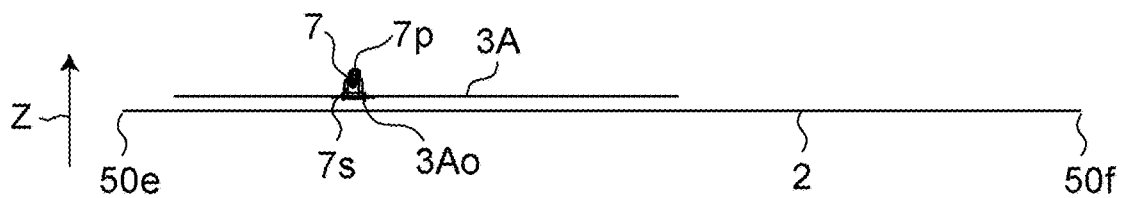
FIG. 14B is a cross-sectional view taken along a line XIVB-XIVB in FIG. 14A.
Figure 14C:
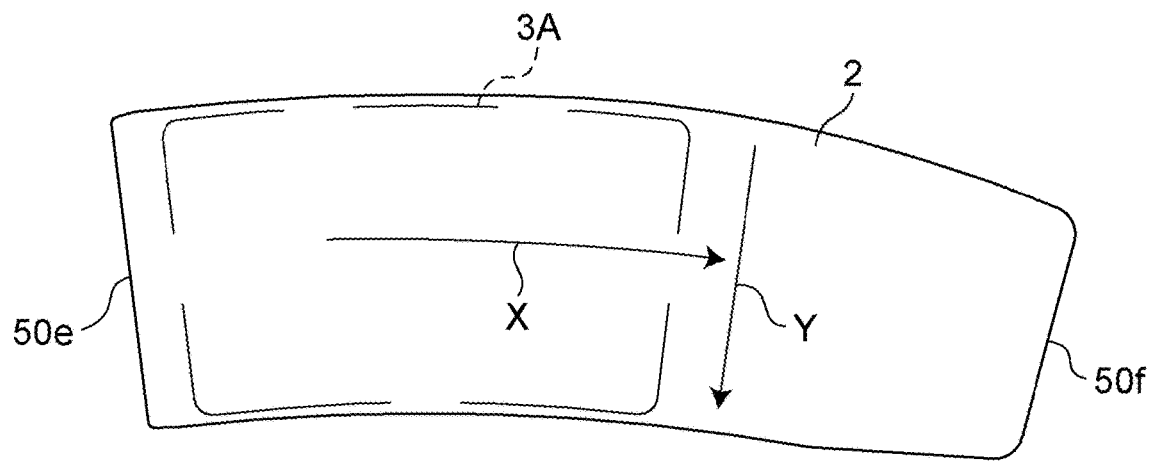
FIG. 14C is a plan view of the blood pressure measurement cuff illustrated in FIG. 14A as viewed from the front surface side of the inner fabric.
Figure 15A:
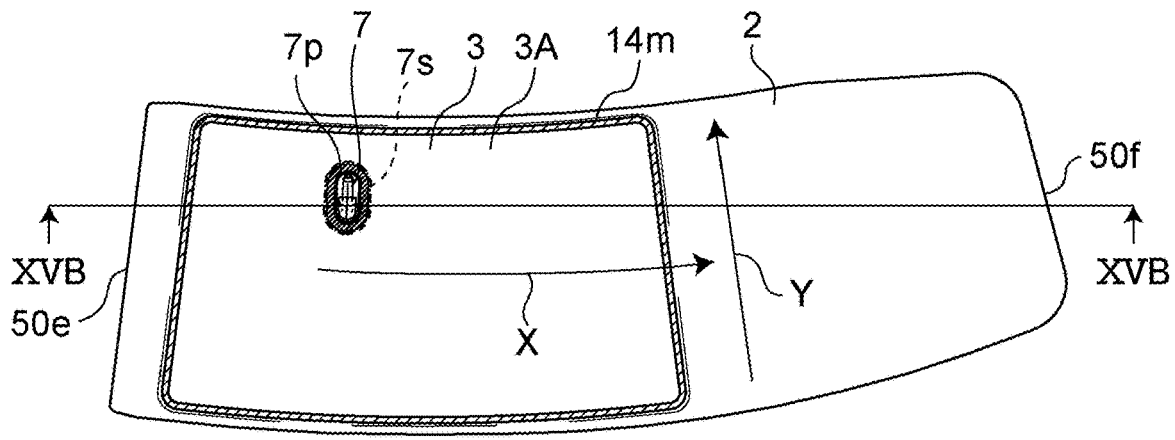
FIG. 15A is a plan view of the blood pressure measurement cuff, as viewed from the back surface side of the inner fabric, for describing the process of attaching, to the back surface of the inner fabric, the nipple and the sheet serving as the fluid bag by welding, the process belonging to the second process of the method for manufacturing the blood pressure measurement cuff.
Figure 15B:
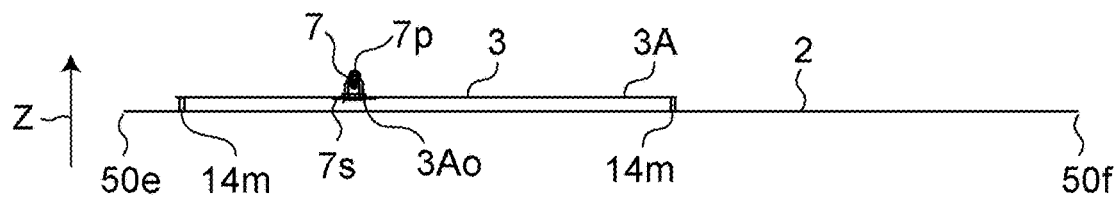
FIG. 15B is a cross-sectional view taken along a line XVB-XVB in FIG. 15A.
Figure 15C:
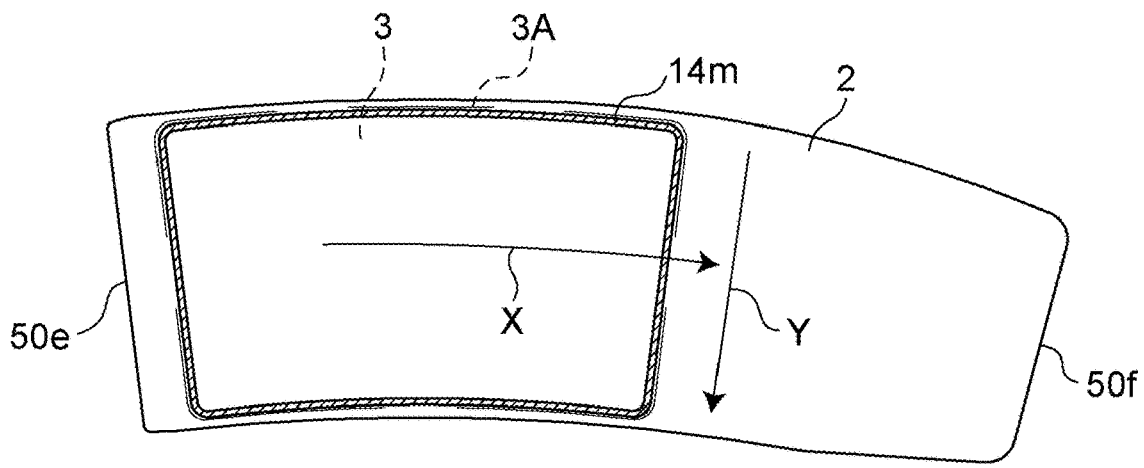
FIG. 15C is a plan view of the blood pressure measurement cuff illustrated in FIG. 15A as viewed from the front surface side of the inner fabric.

In step S2 of FIG. 5 (second process), first, as illustrated in FIGS. 13A and 13B, the nipple 7 is aligned with the sheet 3A. Specifically, in this example, the flange-like support part 7s of the nipple 7 is placed on the front surface (the surface closer to the inner fabric 2 after assembly) around the through hole 3Ao provided in advance of the sheet 3A in the thickness direction Z (from the side in the −Z direction) to cause the cylindrical part 7p of the nipple 7 to project through the through hole 3Ao in the thickness direction Z. In this state, as illustrated in FIGS. 14A and 14B, the flange-like support part 7s of the nipple 7 is welded to the front surface around the through hole 3Ao of the sheet 3A using the welding tool (not illustrated). As a result, the nipple 7 is attached to the sheet 3A. Subsequently, as illustrated in FIGS. 14A, 14B, and 14C, the sheet 3A is aligned with the inner fabric 2. Specifically, in this example, the sheet 3A is placed on the back surface of the inner fabric 2 to face a region that occupies more than half of the region adjacent to the one end 50e in the longitudinal direction X and most of the region in the width direction Y. In this state, as illustrated in FIGS. 15A, 15B, and 15C, the sheet 3A is welded, using the welding tool (not illustrated), to the back surface of the inner fabric 2 along the ring line 14m. As a result, the fluid bag 3 is formed.

Note that, in the above-described example, step S2 (second process) is performed after step S1 (first process), but the present invention is not limited to such an order. Step S1 may be performed after step S2, or step S1 and step S2 may be performed in parallel with each other.

Next, in step S3 of FIG. 5, the belt-like body 50 is formed of the outer fabric 1 and the inner fabric 2 (third process).

Figure 16A:
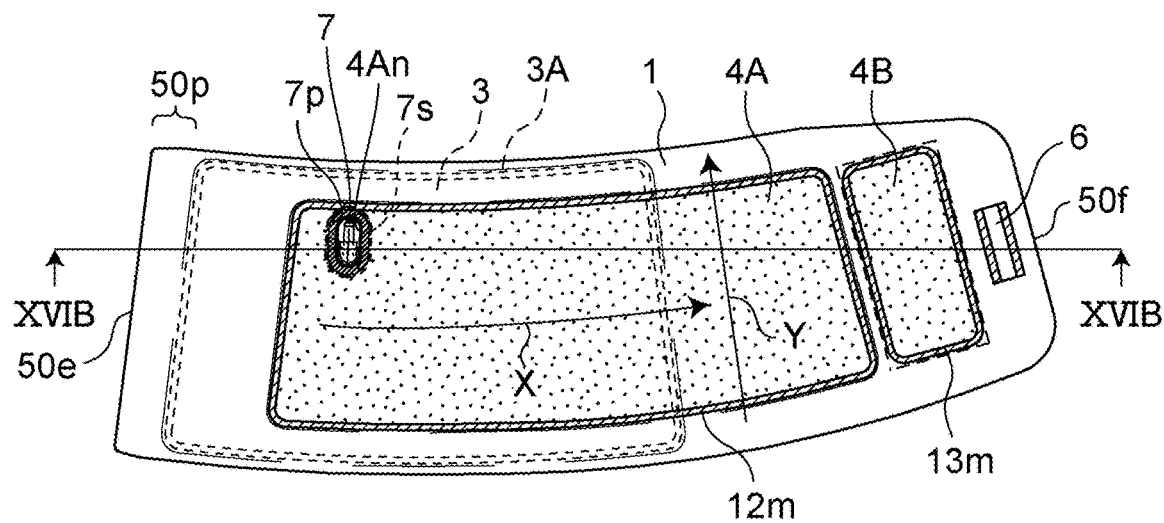
FIG. 16A is a plan view of the blood pressure measurement cuff, as viewed from the outer fabric side, for describing a process of welding the outer fabric and the inner fabric together, the process belonging to a third process of the method for manufacturing the blood pressure measurement cuff.
Figure 16B:
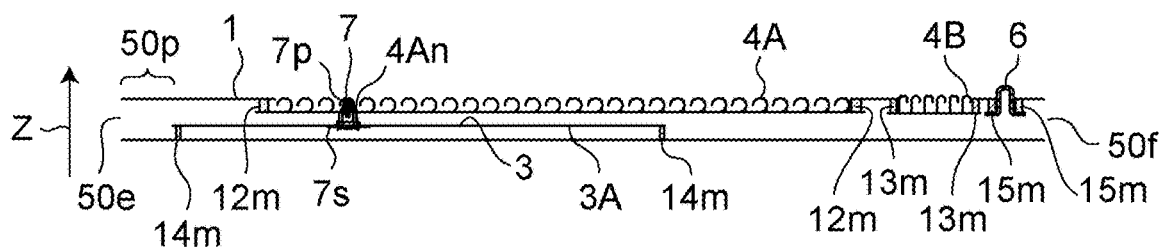
FIG. 16B is a cross-sectional view taken along a line XVIB-XVIB in FIG. 16A.
Figure 16C:
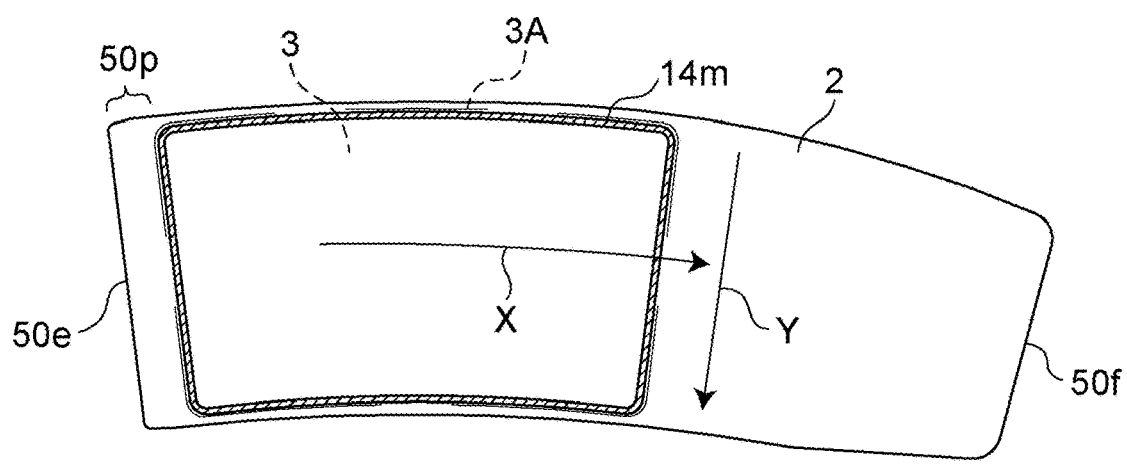
FIG. 16C is a plan view of the blood pressure measurement cuff illustrated in FIG. 16A as viewed from the inner fabric side.
Figure 17A:
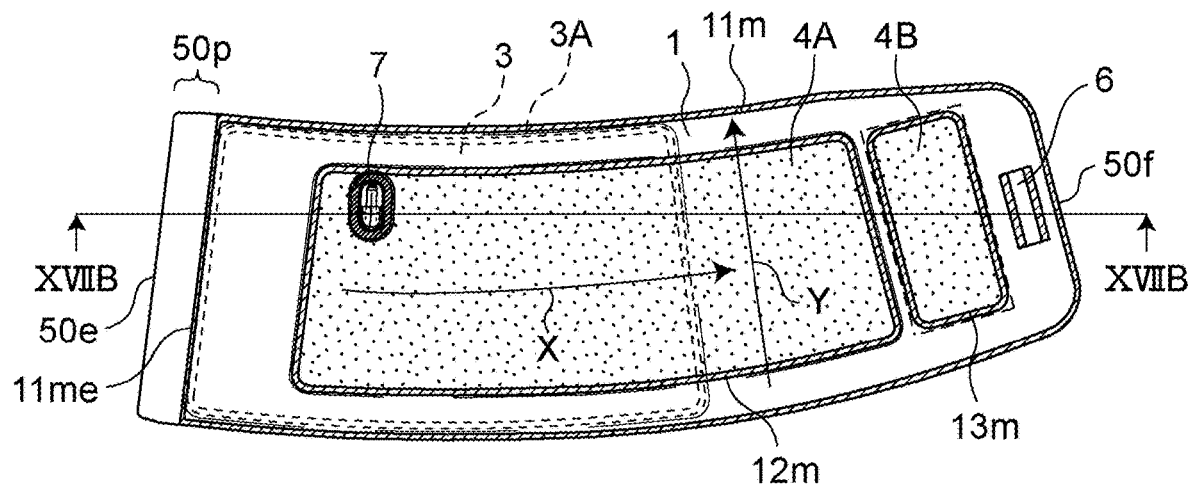
FIG. 17A is a plan view of the blood pressure measurement cuff, as viewed from the outer fabric side, for describing the process of welding the outer fabric and the inner fabric together, the process belonging to the third process of the method for manufacturing the blood pressure measurement cuff.
Figure 17B:
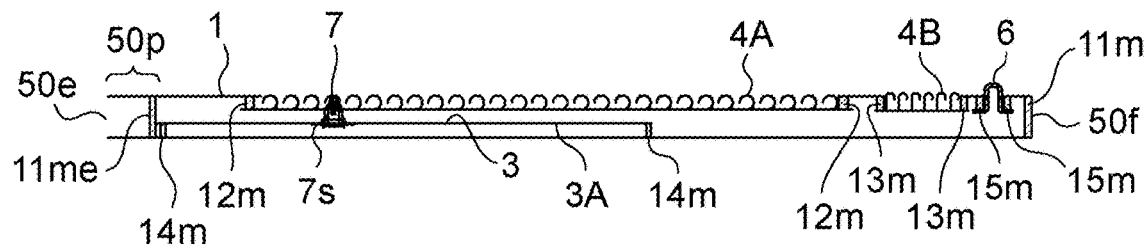
FIG. 17B is a cross-sectional view taken along a line XVIIB-XVIIB in FIG. 17A.
Figure 17C:
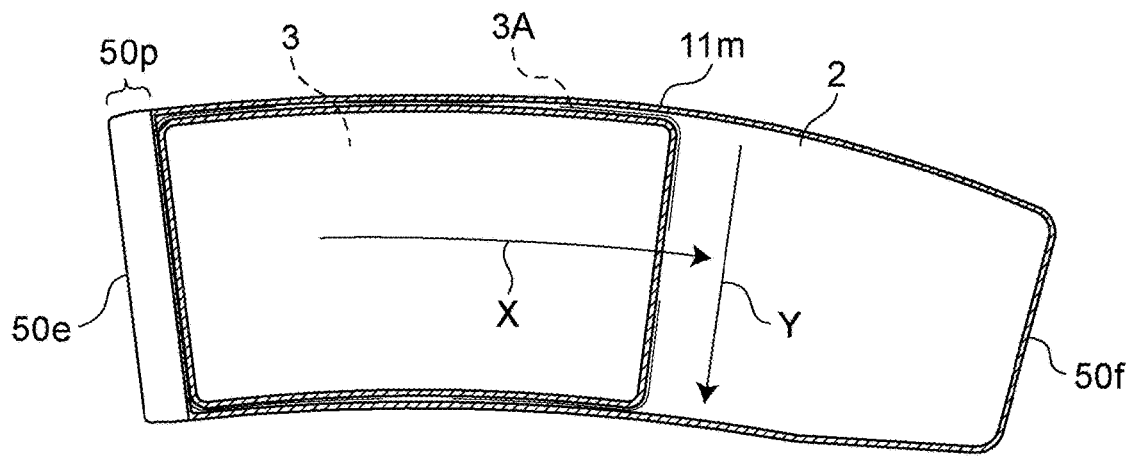
FIG. 17C is a plan view of the blood pressure measurement cuff illustrated in FIG. 17A as viewed from the inner fabric side.

Specifically, first, as illustrated in FIGS. 16A, 16B, and 16C, the outer fabric 1 that has undergone step S1 and the inner fabric 2 that has undergone step S2 are aligned so as to face each other in the thickness direction Z (more specifically, so as to cause the respective back surfaces of the outer fabric 1 and the inner fabric 2 to face each other). Here, FIG. 16A illustrates the pair of the aligned outer fabric 1 and the inner fabric 2 as viewed from the outer fabric 1 side (the same applies to FIGS. 17A and 18A to be described later). FIG. 16B is a cross-sectional view (end view) taken along a line XVIB-XVIB in FIG. 16A (the same applies to FIGS. 17B and 18B with respect to FIGS. 17A and 18A to be described later). Further, FIG. 16C illustrates the pair of the aligned outer fabric 1 and the inner fabric 2 as viewed from the inner fabric 2 side (the same applies to FIGS. 17C and 18C to be described later). At this time, as illustrated in FIGS. 16A and 16B, the cylindrical part 7p of the nipple 7 projects outward through the opening 4An of the hook-and-loop fastener 4A in the thickness direction Z. In this state, as illustrated in FIGS. 17A, 17B, and 17C, with the fluid bag 3 housed, their respective parts near the peripheries of the outer fabric 1 and the inner fabric 2 are welded together, using the welding tool (not illustrated), along the ring line 11m so as to leave the region 50p adjacent to the one end 50e. As a result, the belt-like body 50 is formed in a bag shape. Not that the welded line 11m passes through a region (welded region 11me) located away from the one end 50e of the belt-like body 50 by the size of the region 50p in the +X direction.

In the above-described third process, simply stacking the outer fabric 1 and the inner fabric 2 in the thickness direction Z allows (cylindrical part 7p of) the nipple 7 to pass through the opening 4An. As a result, the process of combining the outer fabric 1 and the inner fabric 2 is simplified (suitable for automation) because the process is performed in the thickness direction Z.

Next, in step S4 of FIG. 5, the elliptical ring member 5 is attached to the region 50p adjacent to the one end 50e of the belt-like body 50 (fourth process).

Figure 18A:
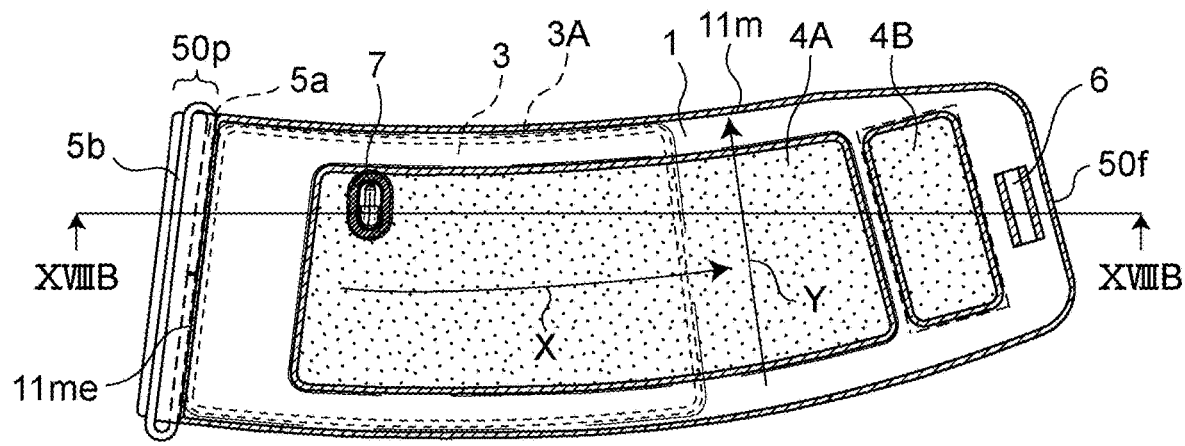
FIG. 18A is a plan view of the blood pressure measurement cuff, as viewed from the outer fabric side, for describing a process of attaching, to a region adjacent to one end of a belt-like body, a ring member by welding, the process belonging to a fourth process of the method for manufacturing the blood pressure measurement cuff.
Figure 18B:
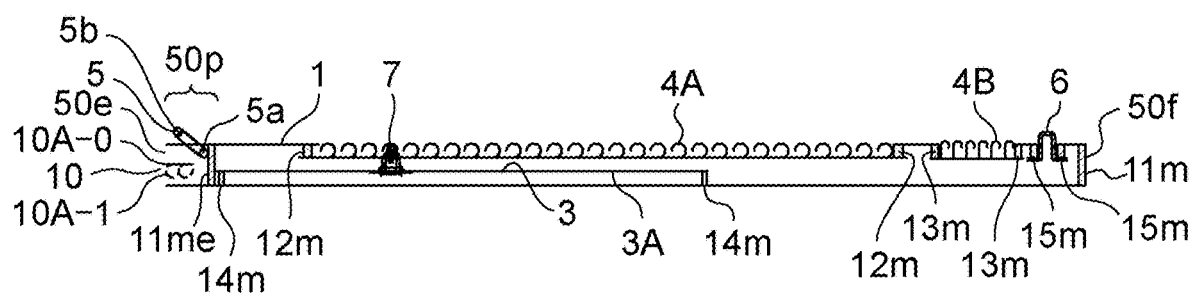
FIG. 18B is a cross-sectional view taken along a line XVIIIB-XVIIIB in FIG. 18A.
Figure 18C:
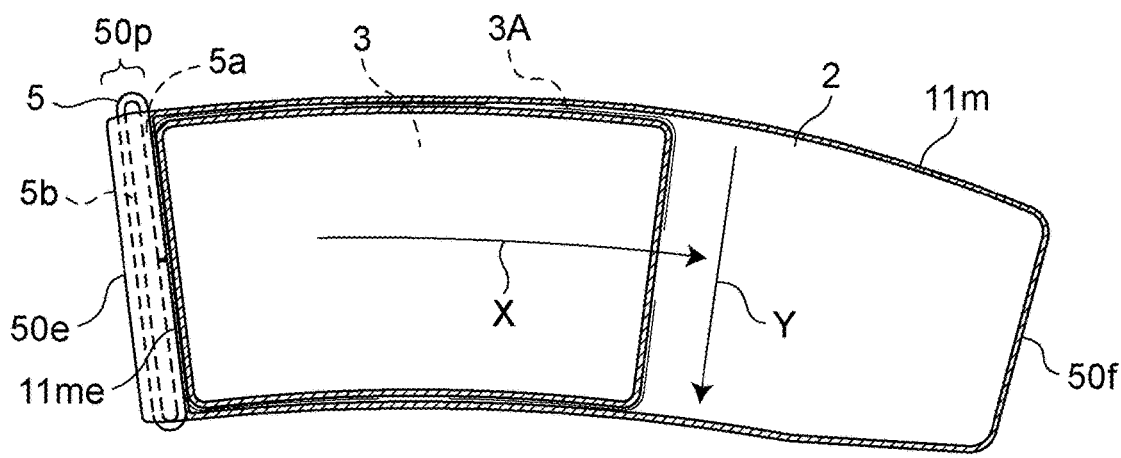
FIG. 18C is a plan view of the blood pressure measurement cuff illustrated in FIG. 18A as viewed from the inner fabric side.

Specifically, first, as illustrated in FIGS. 18A, 18B, and 18C, the one side 5a of the ring member 5 is placed between the outer fabric 1 and the inner fabric 2 in the region 50p adjacent to the one end 50e of the belt-like body 50 along the welded region 11me. At this time, the other side 5b of the ring member 5 is placed on the outside (front surface side) of the outer fabric 1. Further, at this time, the reinforcing layer 10 (the same member as the loop-like hook-and-loop fastener 4A) is placed between the outer fabric 1 and the inner fabric 2 in the region 16m corresponding to a region between the one end 50e and the one side 5a of the ring member 5. In this state, as illustrated in FIGS. 1, 2, and 3, the outer fabric 1, the inner fabric 2, and the reinforcing layer 10 are collectively welded, using the welding tool (not illustrated), in the region (welded region) 16m corresponding to the region between the one end 50e and the one side 5a of the ring member 5. As a result, the one side 5a of the elliptical ring member 5 is attached, along a direction intersecting the belt-like body 50, to the region 50p adjacent to the one end 50e of the belt-like body 50 with the one side 5a interposed between the outer fabric 1 and the inner fabric 2. This makes the ring member 5 rotatable about the one side 5a relative to the belt-like body 50.

In the above-described fourth process, the process of placing the ring member 5 and the reinforcing layer 10 in the region 50p adjacent to the one end 50e of the belt-like body 50 includes movement in the plane direction of the belt-like body 50. At the placement phase, however, since the one end 50e of the belt-like body 50 is an open end (the outer fabric 1 and the inner fabric 2 are not welded), the difficulty of the process is relatively small. The process of collectively welding the outer fabric 1, the inner fabric 2, and the reinforcing layer 10 can be easily performed because the process is performed in the thickness direction Z.

Further, in the above-described fourth process, the reinforcing layer 10 is attached to the belt-like body 50 together with the ring member 5. This prevents an excessive increase in the number of processes due to the process of providing the reinforcing layer 10.

As described above, this manufacturing method allows the above-described foldable blood pressure measurement cuff 100 to be easily assembled by welding. In particular, this method for manufacturing the blood pressure measurement cuff 100 is suitable for automation because the method mainly includes the processes performed on the belt-like body 50 (the outer fabric 1, the inner fabric 2) in the thickness direction Z.

(Actions and Effects During Use)

The above-described foldable blood pressure measurement cuff 100 has the following actions and effects during use.

Figure 19A:
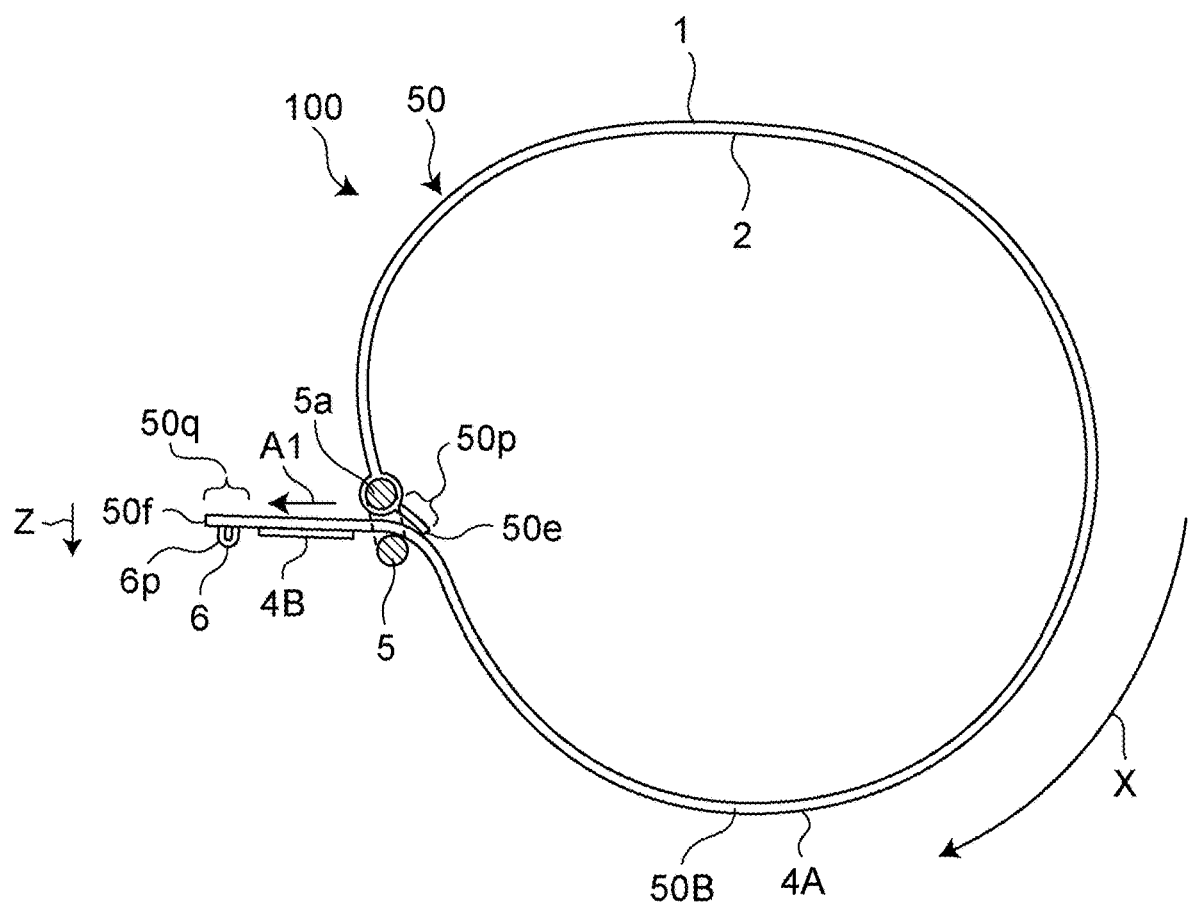
FIG. 19A is a diagram for describing how to attach the blood pressure measurement cuff to a left upper arm as a measurement part.

When the blood pressure measurement cuff 100 is attached to the measurement part (for example, the left upper arm 90), with the outer fabric 1 positioned on the outer circumferential side and the inner fabric 2 positioned on the inner circumferential side, a part (including the retaining member 6) contiguous with the other end 50f of the belt-like body 50 is inserted through the ring member 5 as indicated by an arrow A1 in FIG. 19A. This makes the belt-like body 50 substantially cylindrical. At this time, in the blood pressure measurement cuff 100, the cross section of the projection part 6p of the retaining member 6 in the longitudinal direction X has an inverted U shape with a rounded distal end in the thickness direction Z. Therefore, when pushed from the outside in the thickness direction Z, the projection part 6p of the retaining member 6 is easily dented. Therefore, when the belt-like body 50 is made substantially cylindrical for attachment to the measurement part, the part (including the retaining member 6) contiguous with the other end 50f of the belt-like body 50 is easily inserted through the ring member 5.

Further, once the retaining member 6 is inserted through the ring member 5, even when the part contiguous with the other side 50f of the belt-like body 50 moves backward due to a weight of a non-inserted part (a part not inserted through the ring member 5) 50B of the belt-like body 50, the retaining member 6 prevents the other end 50f of the belt-like body 50 from falling out of the ring member 5. This is because, as described above, the thickness from the front surface of the inner fabric 2 to the distal end of the projection part 6p (about 8 mm in this example) is set larger than the gap between the sides 5a, 5b of the ring member 5 (about 7 mm in this example).

Figure 19B:
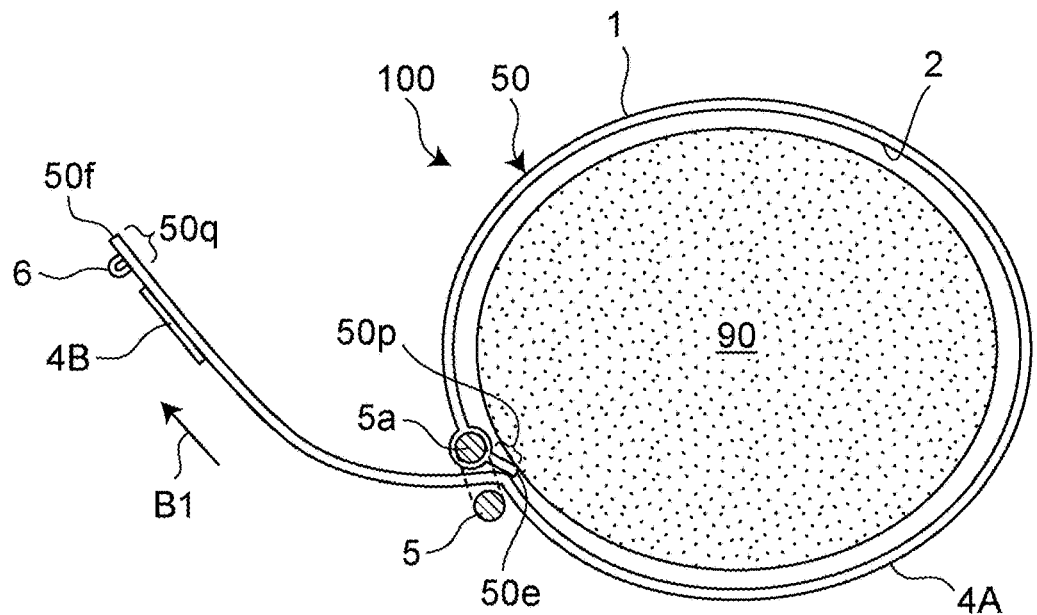
FIG. 19B is a diagram for describing how to attach the blood pressure measurement cuff to the left upper arm.

Next, as indicated by an arrow B1 in FIG. 19B, the left upper arm 90 is passed through this cylindrical belt-like body 50, and the part contiguous with the other end 50f of the belt-like body 50 is first pulled away from the left upper arm toward the left side of the body by the right hand. At this time, since the reinforcing layer 10 (see FIG. 2) is provided to the region 50p adjacent to the one end 50e of the belt-like body 50, the region 50p adjacent to the one end 50e of the belt-like body 50 is prevented from being bent and caught by the measurement part, that is, the skin (upward in FIG. 19B).

Figure 19C:
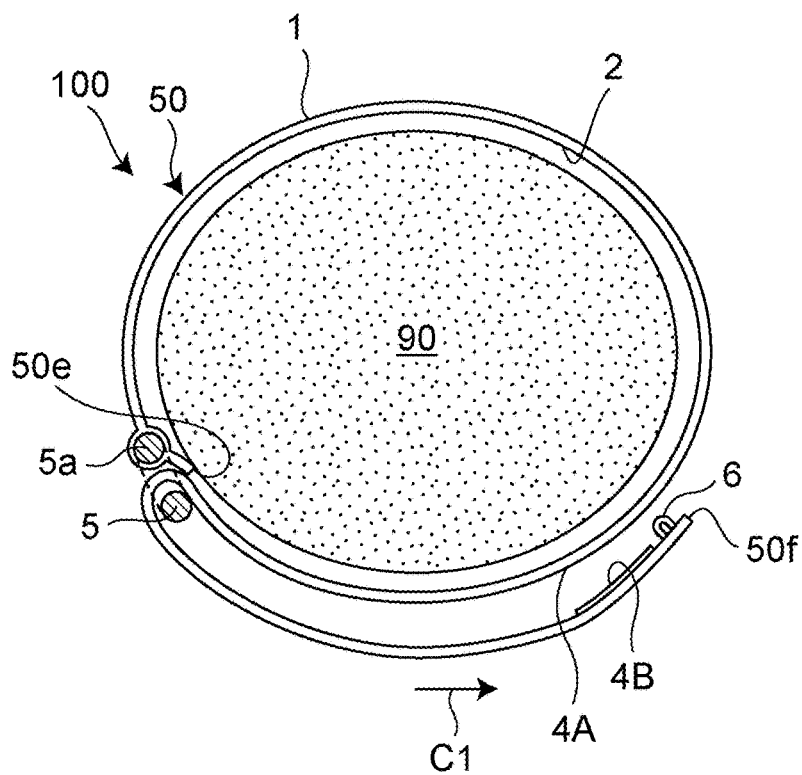
FIG. 19C is a diagram for describing a state where the blood pressure measurement cuff has been attached to the left upper arm.

Subsequently, as indicated by an arrow C1 in FIG. 19C, the part contiguous with the other end 50f of the belt-like body 50 is folded back. Then, the hook-like hook-and-loop fastener 4B near the other end 50f of the belt-like body 50 is engaged with the loop-like hook-and-loop fastener 4B provided on the front surface of the opposite outer fabric 1. As a result, the part that is contiguous with the other end 50f of the belt-like body 50 and folded back through the ring member 5 is fixed to the opposite part of the outer fabric 1 (completion of attachment).

During blood pressure measurement, a fluid (typically air) is supplied to the fluid bag 3 from the outside of the belt-like body 50 through the nipple 7 to compress the left upper arm 90. As a result, blood pressure is measured, for example, by the oscillometric method.

(Variations)

In the above-described embodiment, the retaining member 6 is attached to the belt-like body 50 by welding the support parts 6s, 6s of the retaining member 6 to the back surface around the end opening 1C of the outer fabric 1, but the present invention is not limited to such a method.

For example, the end opening 1C may be provided to the region 50q adjacent to the other end 50f of the belt-like body 50 to penetrate the outer fabric 1 and the inner fabric 2, and the retaining member 6 may be attached so as to cause the projection part 6p to project outward in the thickness direction Z from the inner fabric 2 toward the outer fabric 1 through the end opening 1C. In this case, the support parts 6s, 6s of the retaining member 6 are collectively welded to the part around the end opening 1C of the outer fabric 1 and the inner fabric 2 from the side in the −Z direction (that is, from the inner fabric 2).

Figure 20A:
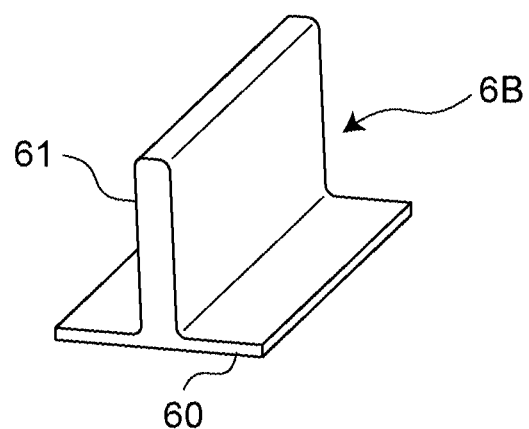
FIG. 20A is a perspective view of a variation of the retaining member.
Figure 20B:
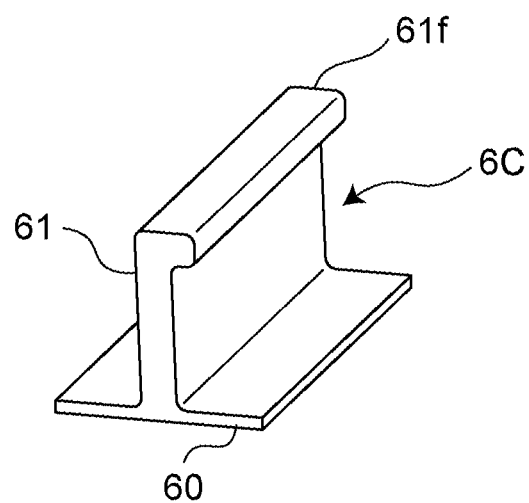
FIG. 20B is a perspective view of another variation of the retaining member.

Further, the retaining member 6 is not limited to the type (see FIG. 4A) in which the cross section of the above-described projection part 6p in the longitudinal direction X has an inverted U shape. For example, as illustrated in FIG. 20A, the retaining member (denoted by a reference numeral 6B) may be of a type having a flat plate-like support part 60 and a flat plate-like projection part 61 provided to stand in the center of the flat plate-like support part 60. Alternatively, as illustrated in FIG. 20B, the retaining member (denoted by a reference numeral 6C) may be of a type having a flat plate-like support part 60 and a flat plate-like projection part 61 provided to stand in the center of the flat plate-like support part 60, and having a distal end of the projection part 61 bent in a direction parallel to the support part 60.

Further, in the belt-like body 50, the reinforcing layer 10 in the region 50p adjacent to one end 50e may be omitted. That is, only the outer fabric 1 and the inner fabric 2 may be welded in the region (welded region) 16m corresponding to a region between the one end 50e and the one side 5a of the ring member 5 to attach the one side 5a of the ring member 5 to the belt-like body 50. This allows a reduction in manufacturing cost.

Note that the measurement part may be an upper limb or a lower limb other than the left upper arm.

As described above, a blood pressure measurement cuff according to the present disclosure is a blood pressure measurement cuff that is foldable and wound around a measurement part to compress the measurement part, the blood pressure measurement cuff including a belt-like body including an outer fabric and an inner fabric facing each other to form a bag shape, the belt-like body housing a fluid bag, an elliptical ring member having one side attached, along a direction intersecting the belt-like body, to a region adjacent to one end of the belt-like body in a longitudinal direction corresponding to a circumferential direction of the measurement part, a retaining member provided to a region adjacent to an other end of the belt-like body opposite from the one end, and a fixing member provided to a front surface of the outer fabric of the belt-like body, the fixing member fixing a part contiguous with the other end of the belt-like body that is folded back through the elliptical ring member when attached to an opposite part of the outer fabric. An end opening is provided to the region adjacent to the other end of the outer fabric, and the retaining member includes a projection part that is flexible and projects, in a thickness direction, outward of the belt-like body from a back surface of the outer fabric through the end opening, and support parts, each being flat plate-like, contiguous with a base of the projection part, and welded to the back surface around the end opening of the outer fabric along the region adjacent to the other end.

Herein, the "outer fabric" and the "inner fabric" that make up the belt-like body refer to fabrics positioned on the outer circumferential side and the inner circumferential side, respectively, when the belt-like body is wound around the measurement part. The "fabric" is not limited to a knitted fabric, and may be made of one or more layers of resin. The "front surface" of the outer fabric refers to one of the surfaces of the outer fabric that is opposite from the inner fabric. A "back surface" of the outer fabric (to be described later) refers to one of the surfaces of the outer fabric that faces the inner fabric. The outer fabric and the inner fabric may make up all or part of the fluid bag.

The "longitudinal direction" of the belt-like body refers to a direction corresponding to the circumferential direction of the measurement part when attached. The "thickness direction" of the belt-like body refers to a direction orthogonal to the plane on which the belt-like body extends. The "one end" and the "other end" of the belt-like body each refer to a true end (one point) in the longitudinal direction.

In the blood pressure measurement cuff according to the present disclosure, the end opening is provided to the region adjacent to the other end of the outer fabric. The retaining member includes the flexible projection part that projects, in a thickness direction, outward of the belt-like body from a back surface of the outer fabric through the end opening, and the flat plate-like support parts, each being contiguous with the base of the projection part and welded to the back surface around the end opening of the outer fabric along the region adjacent to the other end. Therefore, in the process of attaching the retaining member to the belt-like body, for example, with the projection part of the retaining member projecting, in the thickness direction, outward of the belt-like body from the back surface of the outer fabric through the end opening, the support parts of the retaining member may be welded to the back surface around the end opening of the outer fabric along the region adjacent to the other end. Accordingly, the process of attaching the retaining member to the belt-like body is simplified (suitable for automation) because the process is performed in the thickness direction. Therefore, such a foldable blood pressure measurement cuff can be easily assembled by welding.

When the blood pressure measurement cuff is attached to the left upper arm as the measurement part, the part (including the retaining member) contiguous with the other end of the belt-like body is inserted through the ring member with the outer fabric positioned on the outer circumferential side and the inner fabric positioned on the inner circumferential side to make the belt-like body substantially cylindrical. At this time, the retaining member prevents the other end of the belt-like body from falling out of the ring member.

Further, in this blood pressure measurement cuff, since the support parts of the retaining member have a flat plate shape as described above, when the support parts of the retaining member are placed on the region adjacent to the other end of the outer fabric with the projection part of the retaining member projecting, in the thickness direction, outward of the belt-like body from the back surface of the outer fabric through the end opening in the process of attaching the retaining member to the belt-like body, the inclination of the outer fabric with respect to the thickness direction becomes gentle. Therefore, the support parts of the retaining member are easily welded to the back surface around the end opening of the outer fabric.

In the blood pressure measurement cuff according to the embodiment, of the outer fabric in the longitudinal direction, a first opening is provided to a center region and a second opening is provided to a region between the first opening and the end opening, the fixing member includes a pair of hook-and-loop fasteners, each occupying a corresponding one of the first opening and the second opening, and the pair of hook-and-loop fasteners have their respective peripheral parts welded to the back surface around the first opening of the outer fabric and the back surface around the second opening of the outer fabric, and the pair of hook-and-loop fasteners have their respective main parts surrounded by the peripheral parts exposed to the front surface of the outer fabric through the first opening and the second opening.

The "pair of hook-and-loop fasteners" refers to a pair of a hook-like hook-and-loop fastener and a loop-like hook-and-loop fastener to be engaged with the hook.

In the blood pressure measurement cuff according to the embodiment, the process of attaching the pair of hook-and-loop fasteners that make up the fixing member is simplified (suitable for automation) because the process is performed on belt-like body in the thickness direction. Further, since the pair of hook-and-loop fasteners have a planar shape, when the peripheral part of each of the pair of hook-and-loop fasteners is placed on a corresponding one of the back surface around the first opening and the back surface around the second opening of the outer fabric, the inclination of the outer fabric with respect to the thickness direction becomes gentle. Therefore, the peripheral part of each of the pair of hook-and-loop fasteners is easily welded to a corresponding one of the back surface around the first opening and the back surface around the second opening of the outer fabric.

In the blood pressure measurement cuff according to the embodiment, a cross section of the projection part of the retaining member in the longitudinal direction has an inverted U shape with a rounded distal end in the thickness direction.

In the blood pressure measurement cuff according to the embodiment, the cross section of the projection part of the retaining member in the longitudinal direction has an inverted U shape with a rounded distal end in the thickness direction. Therefore, when pushed from the outside in the thickness direction, the projection part of the retaining member is easily dented. Therefore, when the belt-like body is made substantially cylindrical for attachment to the measurement part, the part (including the retaining member) contiguous with the other end of the belt-like body is easily inserted through the ring member.

In the blood pressure measurement cuff according to the embodiment, of the belt-like body, a region between the one end and the one side of the ring member is welded with a reinforcing layer interposed between the outer fabric and the inner fabric.

Herein, the "reinforcing layer" refers to a layer higher in bending resistance than the inner fabric and the outer fabric.

In the blood pressure measurement cuff according to the embodiment, when the blood pressure measurement cuff is attached to the measurement part, the region between the one end of the belt-like body and the one side of the ring member can be prevented from being bent and caught by the measurement part, that is, the skin.

According to another aspect, a method for manufacturing a blood pressure measurement cuff according to the present disclosure is a method for manufacturing the blood pressure measurement cuff, the method including a first process and a second process that are performed in parallel with each other or sequentially, the first process being performed on the outer fabric provided with the first opening, the second opening, and the end opening, the second process being performed on the inner fabric, the first process including a process of welding each of the peripheral parts of the pair hook-and-loop fasteners to a corresponding one of the back surface around the first opening of the outer fabric and the back surface around the second opening of the outer fabric to expose each of the main parts surrounded by the peripheral parts of the pair hook-and-loop fastener to the front surface of the outer fabric through a corresponding one of the first opening and the second opening, and a process of welding the support parts of the retaining member to the back surface around the end opening of the outer fabric to cause the projection part of the retaining member to project outward of the belt-like body through the end opening in the thickness direction, the second process including a process of welding a stretchable sheet to the back surface of the inner fabric with the stretchable sheet facing the back surface to form the fluid bag, a third process of welding the outer fabric and the inner fabric together with the fluid bag placed between the outer fabric and the inner fabric and the region adjacent to the one end left to form a bag shape as the belt-like body, and a fourth process of attaching, along the direction intersecting the belt-like body, the one side of the elliptical ring member to the region adjacent to the one end of the belt-like body by welding with the one end interposed between the outer fabric and the inner fabric.

The "back surface" of the inner fabric refers to one of the surfaces of the inner fabric that faces the outer fabric.

The method for manufacturing a blood pressure measurement cuff according to the present disclosure allows the above-described foldable blood pressure measurement cuff to be easily assembled by welding. In particular, the method for manufacturing a blood pressure measurement cuff is suitable for automation because the method mainly includes the processes performed on the belt-like body (the outer fabric, the inner fabric) in the thickness direction.

In the method for manufacturing a blood pressure measurement cuff according to the embodiment, in the fourth process, a region between the one end and the one side of the ring member is welded with a reinforcing layer interposed between the outer fabric and the inner fabric.

In the method for manufacturing a blood pressure measurement cuff according to the embodiment, in the fourth process, the reinforcing layer is attached to the belt-like body together with the ring member. This prevents an excessive increase in the number of processes due to the process of providing the reinforcing layer.

According to yet another aspect, a blood pressure measurement cuff according to the present disclosure is a foldable blood pressure measurement cuff that is wound around a measurement part to compress the measurement part, the blood pressure measurement cuff including a belt-like body including an outer fabric and an inner fabric facing each other to form a bag shape, the belt-like body housing a fluid bag, an elliptical ring member having one side attached, along a direction intersecting the belt-like body, to a region adjacent to one end of the belt-like body in a longitudinal direction corresponding to a circumferential direction of the measurement part, a retaining member provided to a region adjacent to an other end of the belt-like body opposite from the one end, and a fixing member provided to a front surface of the outer fabric of the belt-like body, the fixing member fixing a part contiguous with the other end of the belt-like body that is folded back through the elliptical ring member when attached to an opposite part of the outer fabric. An end opening is provided to the region adjacent to the other end of the outer fabric to penetrate the outer fabric and the inner fabric, and the retaining member includes a projection part that is flexible and projects, in a thickness direction, outward of the belt-like body from the inner fabric toward the outer fabric through the end opening, and support parts, each being flat plate-like, contiguous with a base of the projection part, and collectively welded to a part around the end opening of the outer fabric and the inner fabric from a side of the inner fabric along the region adjacent to the other end.

The above embodiments are merely illustrative, and various variations can be made without departing from the scope of the present invention. The plurality of embodiments described above can be implemented separately, but the embodiments can also be combined. Likewise, various features in different embodiments can be implemented separately, but the features in different embodiments can also be combined.

The invention claimed is:

1. A blood pressure measurement cuff that is foldable and wound around a measurement part to compress the measurement part, comprising:
    a belt-like body including an outer fabric and an inner fabric facing each other to form a bag shape, the belt-like body housing a fluid bag;
    an elliptical ring member having one side attached, along a direction intersecting the belt-like body, to a region adjacent to one end of the belt-like body in a longitudinal direction corresponding to a circumferential direction of the measurement part;
    a retaining member attached to a region adjacent to an other end of the belt-like body opposite from the one end; and
    a fixing member attached to a front surface of the outer fabric of the belt-like body, the fixing member fixing a part contiguous with the other end of the belt-like body that is folded back through the elliptical ring member when attached to an opposite part of the outer fabric, wherein
    an end opening is included in the region adjacent to the other end of the outer fabric, and
    the retaining member includes a projection part that is flexible and projects, in a thickness direction, outward of the belt-like body from a back surface of the outer fabric through the end opening, and support parts, each being flat plate-like, contiguous with a base of the projection part, and welded to the back surface around the end opening of the outer fabric along the region adjacent to the other end.

2. The blood pressure measurement cuff according to claim 1, wherein
    of the outer fabric in the longitudinal direction, a first opening is included in a center region and a second opening is included in a region between the first opening and the end opening, the fixing member includes a pair of hook-and-loop fasteners, each occupying a corresponding one of the first opening and the second opening, and the pair of hook-and-loop fasteners have their respective peripheral parts welded to the back surface around the first opening of the outer fabric and the back surface around the second opening of the outer fabric, and the pair of hook-and-loop fasteners have their respective main parts surrounded by the peripheral parts exposed to the front surface of the outer fabric through the first opening and the second opening.

3. The blood pressure measurement cuff according to claim 1, wherein a cross section of the projection part of the retaining member in the longitudinal direction has an inverted U shape with a rounded distal end in the thickness direction.

4. The blood pressure measurement cuff according to claim 1, wherein of the belt-like body, a region between the one end and the one side of the elliptical ring member is welded with a reinforcing layer interposed between the outer fabric and the inner fabric.

5. A blood pressure measurement cuff that is foldable and wound around a measurement part to compress the measurement part, comprising:

a belt-like body including an outer fabric and an inner fabric facing each other to form a bag shape, the belt-like body housing a fluid bag;

an elliptical ring member having one side attached, along a direction intersecting the belt-like body, to a region adjacent to one end of the belt-like body in a longitudinal direction corresponding to a circumferential direction of the measurement part;

a retaining member attached to a region adjacent to an other end of the belt-like body opposite from the one end; and a fixing member attached to a front surface of the outer fabric of the belt-like body, the fixing member fixing a part contiguous with the other end of the belt-like body that is folded back through the elliptical ring member when attached to an opposite part of the outer fabric, wherein an end opening is included in the region adjacent to the other end of the outer fabric to penetrate the outer fabric and the inner fabric, and the retaining member includes a projection part that is flexible and projects, in a thickness direction, outward of the belt-like body from the inner fabric toward the outer fabric through the end opening, and support parts, each being flat plate-like, contiguous with a base of the projection part and collectively welded to a part around the end opening of the outer fabric and the inner fabric from a side of the inner fabric along the region adjacent to the other end.

\* \* \* \* \*